(12) United States Patent
Arnim et al.

(10) Patent No.: US 9,314,587 B2
(45) Date of Patent: Apr. 19, 2016

(54) RETROGRADE CARDIOPLEGIA DELIVERY CATHETER AND METHOD FOR INDUCING CARDIOPLEGIC ARREST

(75) Inventors: Nathan Arnim, Salt Lake City, UT (US); Matthew Hellewell, Lehi, UT (US)

(73) Assignee: Edwards Lifesciences Corporation, Irvine, CA (US)

( * ) Notice: Subject to any disclaimer, the term of this patent is extended or adjusted under 35 U.S.C. 154(b) by 665 days.

(21) Appl. No.: 13/449,544

(22) Filed: Apr. 18, 2012

(65) Prior Publication Data

US 2013/0281979 A1    Oct. 24, 2013

(51) Int. Cl.
*A61M 25/10*    (2013.01)
*A61M 25/00*    (2006.01)
*A61M 25/01*    (2006.01)

(52) U.S. Cl.
CPC ....... *A61M 25/0053* (2013.01); *A61M 25/0136* (2013.01); *A61M 25/0147* (2013.01); *A61M 25/007* (2013.01); *A61M 25/0026* (2013.01); *A61M 25/0052* (2013.01); *A61M 25/0105* (2013.01); *A61M 25/0108* (2013.01); *A61M 25/0133* (2013.01); *A61M 25/10* (2013.01); *A61M 2025/0001* (2013.01); *A61M 2025/015* (2013.01); *A61M 2210/125* (2013.01)

(58) Field of Classification Search
CPC ............. A61M 2025/0001; A61M 2025/0002; A61M 2025/0024; A61M 2025/004; A61M 2025/105; A61M 2025/1052; A61M 25/0026; A61M 25/0029; A61M 25/0052; A61M 25/0053; A61M 25/0105; A61M 25/0133; A61M 25/0136; A61M 25/0147; A61M 25/10; A61M 25/104; A61M 25/0108; A61M 25/007
See application file for complete search history.

(56) References Cited

U.S. PATENT DOCUMENTS

| | | | |
|---|---|---|---|
| 4,648,384 A | 3/1987 | Schmukler | |
| 5,021,045 A | 6/1991 | Buckberg et al. | |
| 5,168,864 A * | 12/1992 | Shockey | 600/144 |
| 5,279,597 A | 1/1994 | Dassa et al. | |
| 5,558,644 A | 9/1996 | Boyd et al. | |

(Continued)

FOREIGN PATENT DOCUMENTS

| | | |
|---|---|---|
| WO | 95/08364 A1 | 3/1995 |
| WO | 96/40347 A1 | 12/1996 |

OTHER PUBLICATIONS

Int'. Search Report for PCT/US2013/036988, Jul. 29, 2013.

(Continued)

*Primary Examiner* — Kami A Bosworth
*Assistant Examiner* — Nilay Shah
(74) *Attorney, Agent, or Firm* — Richard B. Cates

(57) ABSTRACT

A retrograde delivery catheter includes at its distal end an expandable member configured to at least partially occlude the coronary sinus of a patient's heart, and has a length and variable stiffness that allows the distal end to be selectively articulated so as to be positioned in the coronary sinus. The delivery catheter has a triple lumen construction with a primary lumen extending between the proximal and distal ends and configured to allow a cardioplegic fluid to be delivered to the coronary sinus. A second lumen provides for balloon inflation while a third lumen allows monitoring of a pressure within the coronary sinus. A torque may be applied and a reinforcement member within the delivery catheter provides improved torque transmission along the length of the catheter.

38 Claims, 11 Drawing Sheets

(56) References Cited

U.S. PATENT DOCUMENTS

| | | | |
|---|---|---|---|
| 5,569,184 A * | 10/1996 | Crocker et al. | 604/509 |
| 5,584,803 A | 12/1996 | Stevens et al. | |
| 5,695,457 A * | 12/1997 | St. Goar et al. | 604/4.01 |
| 5,779,685 A | 7/1998 | Thompson et al. | |
| 5,879,499 A * | 3/1999 | Corvi | A61M 25/0012 156/173 |
| 6,017,323 A * | 1/2000 | Chee | A61M 25/104 604/249 |
| 7,037,290 B2 * | 5/2006 | Gardeski | A61M 25/0147 604/95.01 |
| 2003/0144657 A1 * | 7/2003 | Bowe et al. | 606/41 |
| 2004/0249337 A1 | 12/2004 | DiFiore | |
| 2006/0184106 A1 * | 8/2006 | McDaniel et al. | 604/95.04 |
| 2007/0225641 A1 * | 9/2007 | Schneider et al. | 604/93.01 |
| 2008/0015625 A1 | 1/2008 | Ventura et al. | |
| 2008/0154136 A1 * | 6/2008 | Webler | A61B 8/0833 600/463 |
| 2009/0287135 A1 * | 11/2009 | Michishita et al. | 604/6.16 |

OTHER PUBLICATIONS

Supplementary Partial European Search Report for EP13778671, Dec. 8, 2015.

* cited by examiner

RETROGRADE CARDIOPLEGIA DELIVERY CATHETER AND METHOD FOR INDUCING CARDIOPLEGIC ARREST

BACKGROUND

1. Field of the Invention

This invention relates generally to devices and techniques for performing cardiac procedures and particularly a catheter system and methods for inducing cardioplegic arrest to facilitate the performance of cardiac procedures.

2. The Related Technology

Known techniques for performing major surgeries such as coronary artery bypass grafting and heart valve repair and replacement have generally required open access to the thoracic cavity through a large open wound, known as a thoracotomy. Typically, the sternum is cut longitudinally (i.e., a median sternotomy), providing access between opposing halves of the anterior portion of the rib cage to the heart and other thoracic vessels and organs. An alternate method of entering the chest is via a lateral thoracotomy, in which an incision, typically 10 cm to 20 cm in length, is made between two ribs. A portion of one or more ribs may be permanently removed to optimize access.

In procedures requiring a median sternotomy or other type of thoracotomy, the ascending aorta is readily accessible for placement of an external cross-clamp, and for introduction of a cardioplegic fluid delivery cannula and venting cannula through the aortic wall. However, such surgery often entails weeks of hospitalization and months of recuperation time, in addition to the pain and trauma suffered by the patient. Moreover, while the average mortality rate associated with this type of procedure is about two to fifteen percent for first-time surgery, mortality and morbidity are significantly increased for reoperation. Further, significant complications may result from such procedures. For example, application of an external cross-clamp to a calcified or atheromatous aorta may cause the release of emboli into the brachiocephalic, carotid or subclavian arteries with serious consequences such as strokes.

A less invasive surgical approach is preferred as an alternative to open-chest surgery. During a minimally invasive surgical procedure, a surgeon may access a body lumen such as the femoral artery or jugular, and extend one or more elements through the vasculature of the patient so as to access a location remote from the access window. Devices that may be extended through the access window and to a location of the surgical procedure include catheters, stents, guidewires, or other surgical devices that may be inserted through such an access window for a procedure remote from the access window itself. Thus, a variety of surgical procedures may be performed within the cavities of the body, particularly including minimally invasive and less invasive surgical procedures in which surgical instruments are introduced through an access window, and then extended through body lumens to a desired location.

Methods and devices are therefore needed for isolating the heart and coronary arteries from the remainder of the arterial system, arresting cardiac function, and establishing cardiopulmonary bypass without the open-chest access provided by a median sternotomy or other type of thoracotomy. In particular, methods and devices are needed which facilitate the delivery of retrograde cardioplegia sufficiently to allow the heart to be placed under cardioplegic arrest with full cardiopulmonary bypass, without requiring open-chest access to the heart and without requiring an incision or puncture in the aorta, in the pulmonary artery, or in the heart wall. Embodiments of the present disclosure satisfy these and other needs.

SUMMARY OF THE INVENTION

The present disclosure is directed to a device and method relating to a retrograde cardioplegia delivery catheter. More particularly, embodiments herein relate to a catheter, and methods and systems in which it is used, particularly related to performing cardiac procedures in which the catheter can be used to occlude all or a portion of the coronary sinus.

A retrograde cardioplegia delivery catheter is described herein. An example retrograde delivery catheter may be advanced into a coronary sinus of a patient's heart for retrograde delivery of a fluid. Exemplary delivery catheters may include an elongated shaft having a proximal end and a distal end, with the elongated shaft having sufficient length and flexibility so that the proximal end may extend intraluminally through a patient's peripheral veins when the distal end is positioned in the coronary sinus. The elongated shaft can include multiple layers, including at least an outer shell and an interior reinforcement member, as well as at least two lumens within the shaft. An expandable member is proximate the distal end of the shaft and may be used to at least partially occlude the patient's coronary sinus. The expandable member may further be in fluid communication with at least one of the at least two lumens within the elongated shaft. An outlet port is positioned in communication with a delivery lumen of the at least two lumens, and adapted to deliver a fluid to a location distal to the expandable member.

In some embodiments, a shaft may be an elongated shaft having multiple sections of differing durometer. The shaft may further in some embodiments be a multi-lumen extrusion. Locations of where durometer changes may correspond to inflection points during selective articulation of the elongated shaft.

The reinforcement member is optionally a braided tube. In some embodiments, the reinforcement member may be made of a metal or another material. A material of the reinforcement member may have higher echogenicity and/or radiopacity relative to a material forming an outer shell of a shaft. An interior reinforcement member may also surround a liner of a cardioplegia fluid input.

In another embodiment, a retrograde delivery catheter for retrograde delivery of a fluid into a coronary sinus includes a flexible, elongated shaft having a proximal end and a distal end, the shaft having sufficient length and flexibility so that the proximal end may extend intraluminally through a patient such that when the proximal end is external to the patient, the distal end is positioned in the coronary sinus of the patient. The flexible, elongated shaft may define at least two lumens extending from about the proximal end toward the distal end. An atraumatic distal tip can be included at about the distal end of the flexible, elongated shaft. An expandable member may be positioned at least proximate the distal end of the flexible, elongated shaft, and the expandable member may be configured to at least partially occlude the patient's coronary sinus. A user interface may be coupled to the flexible, elongated shaft, with the user interface being configured to control selective articulation of the distal end of the flexible, elongated shaft. Such articulation may include, by the user interface, articulation that includes at least one pre-set articulation position of the distal end of the flexible, elongated shaft.

The flexible shaft may have a predefined shape that includes an initial bend at the distal end, and/or all positions of the distal end corresponding to the selective articulation of the distal end may be curved. The predetermined positions may include an engagement position that can correspond to a stressed state of the user interface. The predetermined positions may additionally, or alternatively, include insertion or troubleshooting positions of the user interface. At any one or more selected articulations of the distal end of the shaft, the shaft may define multiple sections with differing curvature radii, longitudinal lengths, and/or durometer.

In at least some embodiments, a retrograde delivery catheter includes a pull wire. A pull-wire or other articulation mechanism may be attached to the user interface and to, or near, the distal end of a shaft. The pull-wire may extend through a primary or other lumen within the shaft. A reinforcement member of the shaft may also surround the pull-wire in some embodiments.

To control articulation of the distal end of the shaft, a user interface may include a multi-position switch. The switch may be linked to a pull-wire or other articulation control member. Some positions may be self-sustaining so as to maintain a desired position of the distal end of the shaft even absent continued user pressure. Other positions may not be self-sustaining such that release of user pressure causes the switch to revert to a particular self-sustaining position. Different switch positions may correspond to an insertion position, engagement position, and/or troubleshooting position of the distal end of the shaft. During articulation, the shaft and the distal end of the shaft may remain in-plane.

In accordance with another example embodiment, a method is provided for at least partially occluding a coronary sinus of a patient and delivering retrograde cardioplegia to the coronary sinus. In the method, a retrograde delivery catheter can be used. The catheter may include a flexible shaft having a proximal end and a distal end, the distal end of the shaft being configured to be selectively articulated between at least two pre-determined curve profiles, the shaft defining at least a fluid delivery lumen and an inflation lumen. An expandable member may be positioned at least proximate the distal end of the flexible shaft, the expandable member being inflatable to at least partially occlude the coronary sinus. A user interface may be included and configured to selectively articulate the distal end of the shaft between at least two pre-determined curve profiles. A distal end of the catheter may be introduced into a peripheral vein of a patient, while the distal end of the flexible shaft has a first of at least two pre-determined curve profiles. The distal end may be located in the coronary sinus of the patient. Such locating can include selectively articulating the distal end of the flexible shaft to a second of the at least two predetermined curve profiles and placing the expandable member within the coronary sinus while the proximal end of the shaft remains external to the patient. Fluids can be passed through inflation and delivery lumens to inflate the expandable member and pass into the coronary sinus, respectively. In some aspects, a pressure monitoring lumen may be included in the shaft and the pressure within the coronary sinus can be measured or otherwise monitored at or near the expandable member. Locating the distal end of the catheter may also include articulating the distal end to a position corresponding to a curve profile at which the user interface has a switch that is not self-sustaining. Additionally, or alternatively, a catheter shaft may be concentric relative to an expandable member. Locating the distal end of the retrograde delivery catheter in the coronary sinus of the patient can include limiting eccentricity of the flexible shaft to less than about fifteen percent eccentricity.

These and other advantages of the invention will become more apparent from the following detailed description of the invention when taken in conjunction with the accompanying exemplary drawings. These and other aspects and features of the present invention will become more fully apparent from the following description and appended claims.

BRIEF DESCRIPTION OF THE FIGURES

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures may be drawn to scale for some embodiments, the figures are not necessarily drawn to scale for all embodiments. Embodiments of the present disclosure will be described and explained with additional specificity and detail through the use of the accompanying drawings in which.

DETAILED DESCRIPTION OF EXEMPLARY EMBODIMENTS

Figure 1:
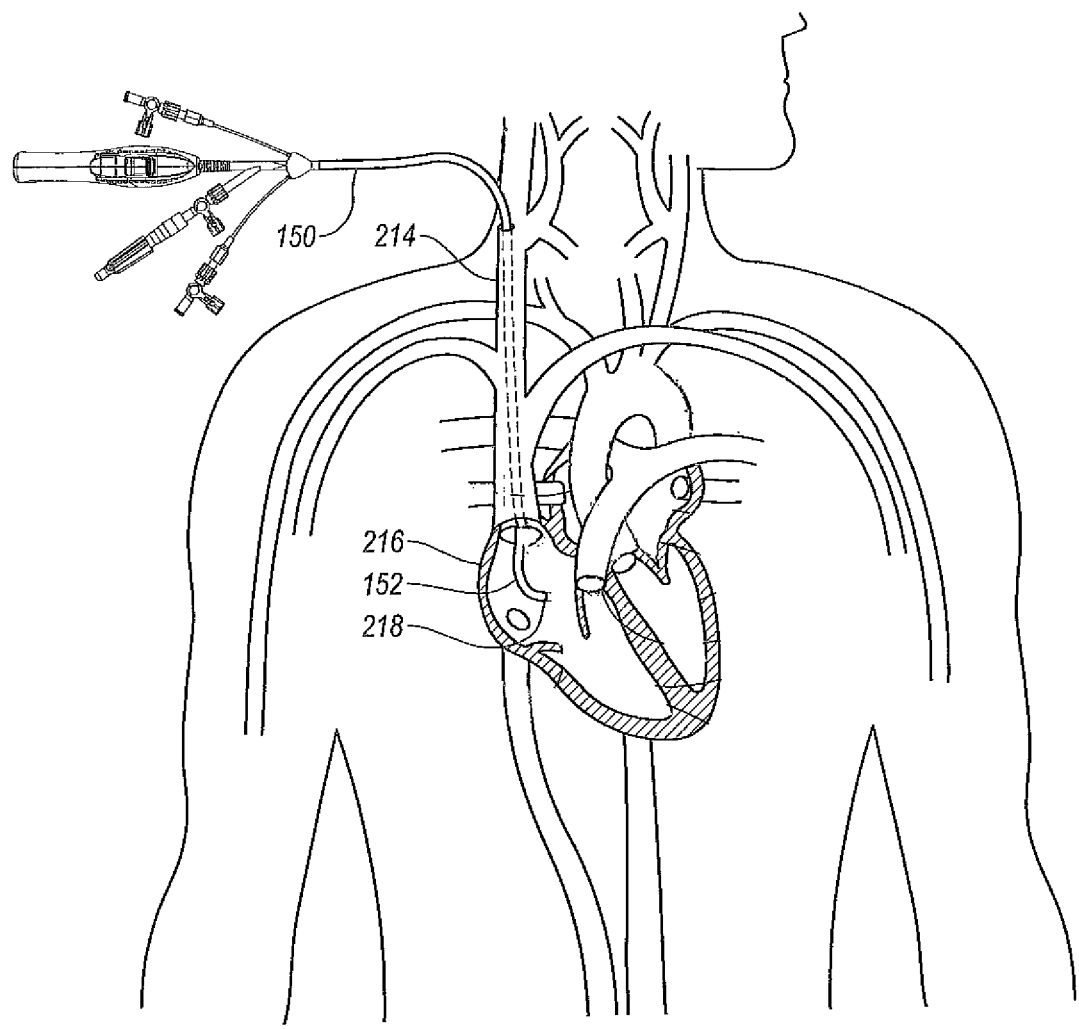
FIG. 1 schematically illustrates a retrograde cardioplegia delivery catheter disposed within the anatomy of a patient according to one example embodiment of the present disclosure.

Exemplary embodiments of the present disclosure are directed to accessing a body lumen in order to perform a medical procedure. Reference is made to FIG. 1, which schematically illustrates the retrograde cardioplegia delivery catheter 150 of the present disclosure.

The retrograde cardioplegia delivery catheter 150 is disposed at least partially within the patient's venous system. In some embodiments, the retrograde cardioplegia delivery catheter 150 may also be configured to occlude a portion of the patient's vasculature and monitor coronary sinus pressure. In at least one embodiment, the catheter 150 extends within the patient's venous system and has a distal section extending into the coronary sinus 212 (see FIG. 2) to deliver a fluid containing cardioplegic agents. The cardioplegic agents can be delivered to the myocardium in a retrograde manner through the patient's coronary venous system, and may be configured to substantially paralyze the myocardium. The cardioplegic agents may also be profused throughout the heart muscle to prevent mild cardio eschemia.

Figure 2:
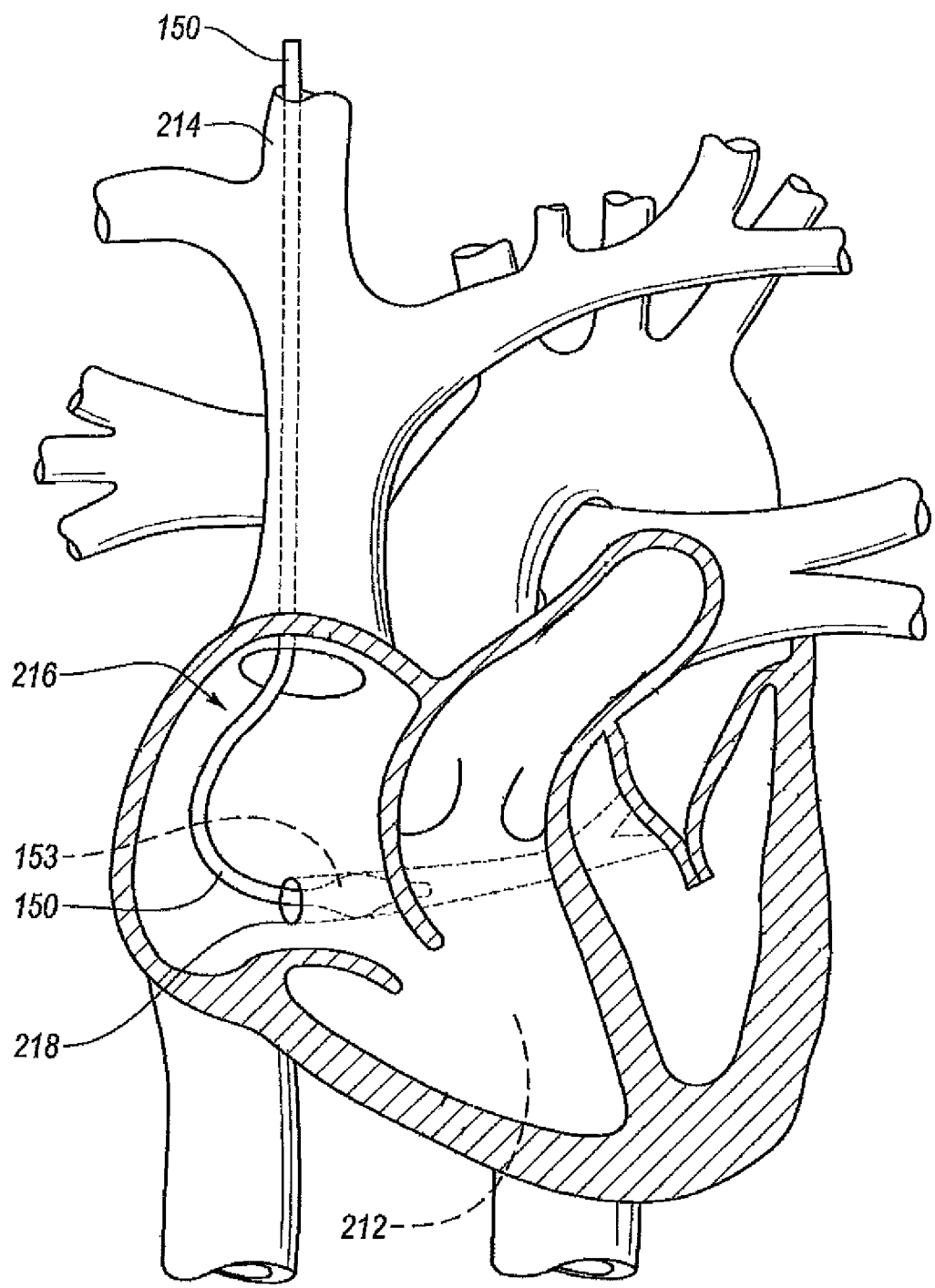
FIG. 2 is a more detailed view of a retrograde cardioplegia delivery catheter disposed within the anatomy of a patient according to one example embodiment of the present disclosure.

An exemplary catheter 150, which may also be seen in FIG. 2, can be introduced into the patient's venous system through the right internal jugular vein 214 and advanced through the right atrium 216 and into the coronary sinus 212 through a coronary sinus discharge opening 218 in the right atrium. Optionally, the retrograde delivery catheter 150 includes a flexible shaft 152 having a distal end having a delivery lumen extending therein. The shaft 152 may have a length sufficient to allow the distal end to be positioned within the coronary sinus while a proximal end of the shaft 152 extends out of the patient, such as through a puncture, cut down, or other access site. As shown in FIG. 1, the access site may access the internal jugular vein 214 of the patient.

The shaft 152 can be flexible so as to allow the catheter 150 to navigate through the patient's vasculature with little difficulty, and preferably in a manner that is suitably atraumatic. A distal end of the shaft 152 may also include an expandable member 153, which may be a balloon configured to expand and occlude the coronary sinus 212. A soft, atraumatic tip may also be located at the distal end of the shaft 152. For instance, the soft distal end may be made of a material having mechanical properties sufficient to reduce a risk of trauma through the vasculature the shaft 152 passes through, including the coronary sinus 212.

In some embodiments, the shaft 152 is made of a biocompatible material. Radiopaque markers may also be applied to the shaft, including at or near the distal end, or a filler such as barium sulfate may be added to the shaft 152. Such markers or the barium sulfate may facilitate visual inspection or placement of the catheter 150. Any of various visualization measures may be utilized. For instance, angioscopic imaging, fluoroscopy, or transesophageal echocardiography may be utilized. In some instances, intravascular ultrasound may be used. For instance, intravascular ultrasound may be used where passed through a delivery catheter, or passed via the venous system through the intra-atrial septum, across the mitral valve, and into the left ventricle.

A liquid containing a cardioplegic agent (e.g., an aqueous saline solution, a potassium chloride, etc.) may be introduced at a proximal end of the delivery catheter 150. The agent may be introduced with sufficient pressure to force the cardioplegic agent through the coronary sinus 212, through the capillary beds (not shown) in the patient's myocardium, through the coronary arteries (not shown) and ostia (not shown). The retrograde cardioplegia delivery catheter 150, can be percutaneously inserted by a suitable means via a introducer sheath (e.g., the Seldinger technique) into the right interior jugular vein 214 and advanced into the right atrium 216 and guided through the discharge opening 218 into the coronary sinus 212.

The expandable member 153 (see FIG. 2) on the distal extremity of the catheter 150 may be expanded to occlude the coronary sinus 212 and thereby prevent or reduce fluid loss through the discharge opening 218 into the right atrium 216. A liquid containing a cardioplegic agent such as potassium chloride may be directed through the catheter 150 into the coronary sinus 212 and the pressure and volumetric flow rate of the cardioplegic fluid within the coronary sinus 212 can be maintained sufficiently high (e.g. at least about 100 ml/min at about 40 mm Hg) so that the cardioplegic fluid will pass through the coronary veins, crossing the capillary beds to the coronary arteries and out the ostia.

Cardioplegic fluid may be delivered through the delivery catheter at a flow rate sufficient to maintain cardioplegic arrest by periodic or continual infusions. However, cardioplegic solution pressure within the coronary sinus 212 may be maintained at a level that avoids or reduces the risk of tissue damage. For instance, the cardioplegic solution pressure may be less than about 50 mm Hg to avoid tissue damage. An example blood-to-agent volumetric ratio is about four parts blood to one part KCl solution. The cardioplegic solution can also be within a desired temperature range. For instance, the cardioplegic solution may be cooled to a temperature of between about 4° C. and about 10° C. Such cooling may result in a fluid having a viscosity in excess of about 3.0 centipoise, and sometimes in the range of about 6 to about 8 centipoise. The cardioplegic fluid may then be directed through a port of the delivery catheter 150 and infused at a desired flow rate (e.g., at least about 100 ml/min or at least about 200 ml/min.) in order to maintain cardioplegic arrest. The pressure at which the fluid is pumped or delivered through the delivery catheter 150 (the "pump pressure") may vary, and in some embodiments is kept around about 350 mmHg so as to avoid excessive hemolysis of the blood component of the fluid and/or damage to the pump. Cardioplegic fluid flow through delivery catheter 150 may be maintained on a periodic basis (e.g., about every 15-30 minutes for 2-4 minutes), so long as the heart remains under cardioplegic arrest.

It will be understood to those of skill in the art in view of the disclosure herein that cardioplegic fluid may be delivered at lower flow rates for longer periods, or more frequently, and potentially continuously, to obtain a same desired total volume of delivered fluid. Delivery at lower flow rates might allow the use of a delivery catheter having a delivery lumen with a reduced cross-sectional area compared to a delivery catheter having higher flow rates. For instance, a catheter for low flow rates may have a minimum area of less than about 4 $mm^2$. In other cases, such as where cardioplegic fluid is delivered less often and/or the time required to deliver the desired volume of cardioplegic fluid is minimized, a delivery lumen cross-sectional area may be larger, while continuing to maintain the overall profile of the catheter 150 small enough to allow transluminal positioning from a peripheral vein.

The present disclosure may also be utilized to induce cardioplegic arrest in conventional open surgical procedures as a substitute for conventional cardioplegia cannula introduced directly into the heart and/or aorta.

Figure 3:
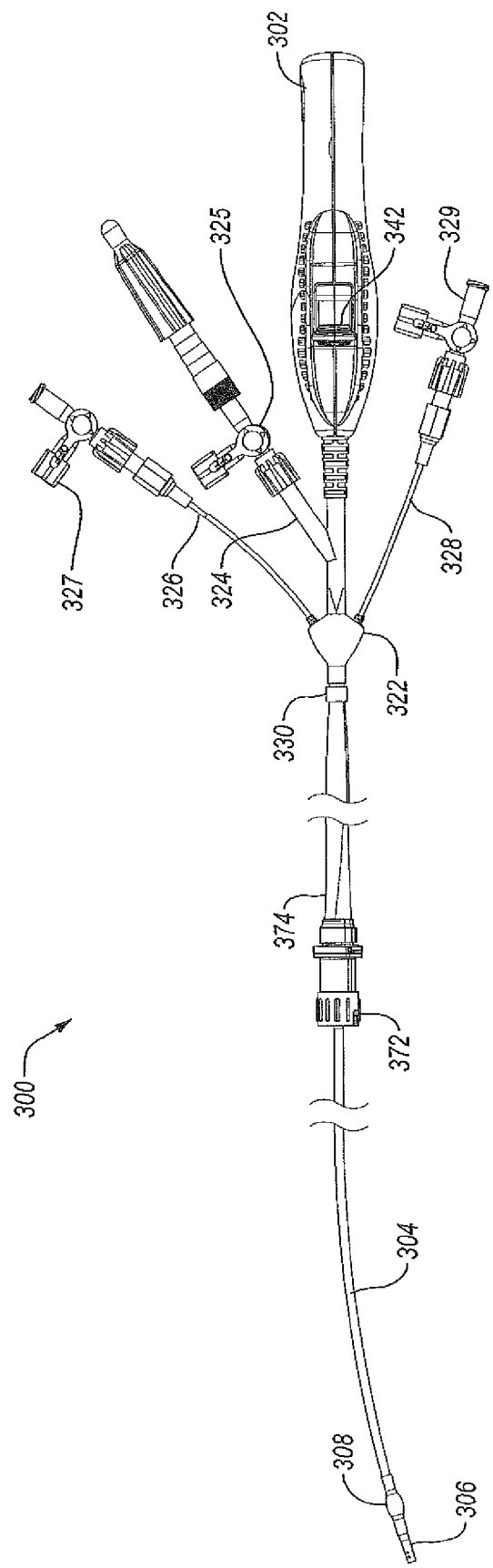
FIG. 3 is a side view of an exemplary retrograde cardioplegia delivery catheter according to one aspect of the present disclosure.

Turning now to FIG. 3, an exemplary embodiment of a delivery catheter, and more particularly a retrograde cardioplegia delivery catheter 300 are illustrated and described in additional detail. In the illustrated embodiment, the delivery catheter 300 includes a catheter shaft 304 that can be inserted into a patient. To facilitate insertion of the shaft, a user interface 302 may be gripped or otherwise manipulated by a surgeon or other user. In accordance with some embodiments disclosed herein, the user interface 302 may used to position the shaft 304 or a distal tip 306 of the shaft 304 at a desired location. For instance, the user interface 302 may be an ergonomic handle that facilitates insertion of the distal tip 306 within the coronary sinus of a patient. The distal portion of the device is optionally articulating, in which articulation is at least partially controlled by the ergonomic user interface 302. Thus, in some embodiments, including those described hereafter, the catheter 300 may be an articulating catheter in which at least a portion of the shaft 304 can be selectively moved or have its shaped selectively changed.

An expandable member 308 is also included in this embodiment, and may be positioned near the distal tip 306. The expandable member 308 may be selectively expanded or contracted, as desired by the surgeon. For instance, the expandable member 308 may be in a retracted state while the distal tip 306 travels to a desired location within a patient. Upon reaching a desired location, such as a coronary sinus, the expandable member 308 may be expanded to fully or partially occlude the coronary sinus.

Figure 4A:
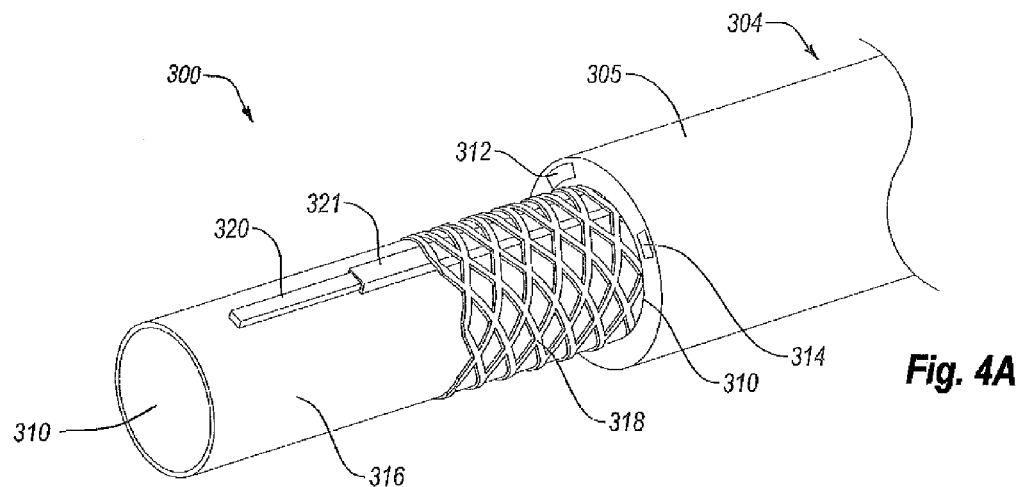
FIG. 4A is a partial cutaway view of a catheter shaft of the retrograde cardioplegia delivery catheter of FIG. 3.
Figure 4B:
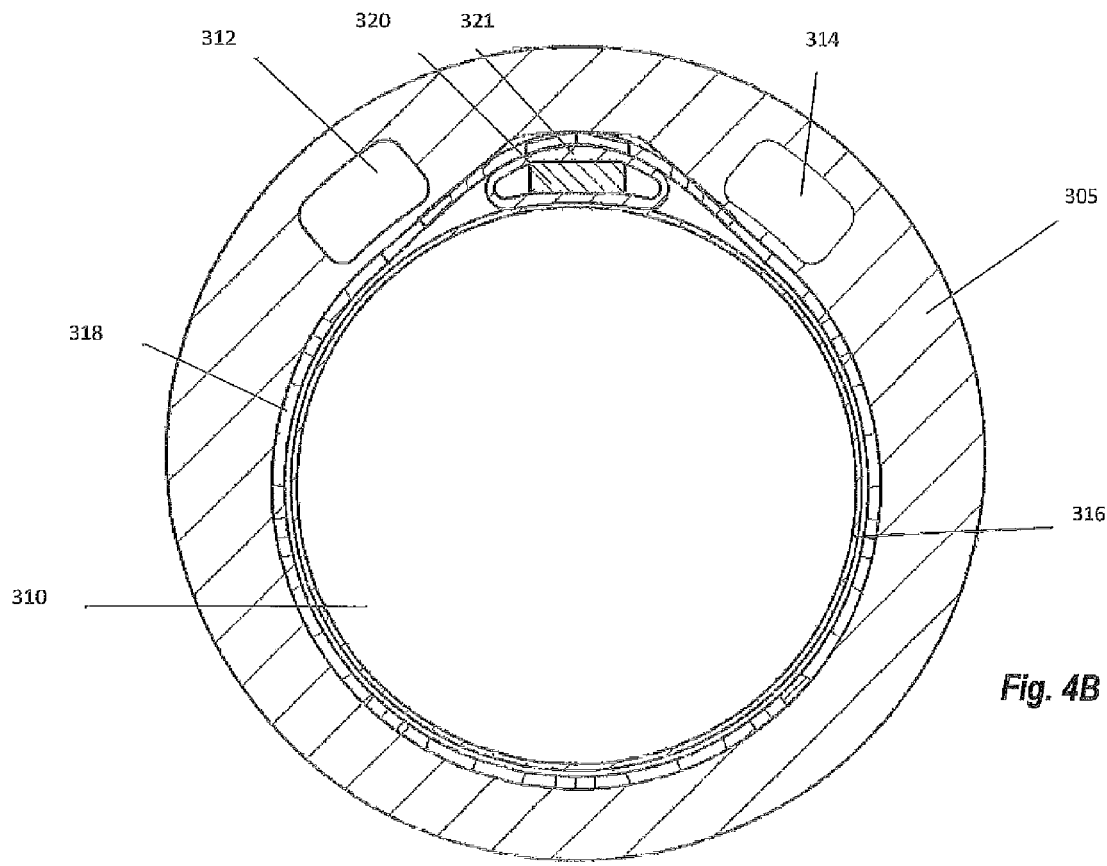
FIG. 4B is a transverse cross-sectional view of the exemplary retrograde cardioplegia delivery catheter of FIG. 3.

As best illustrated in FIGS. 4A and 4B, the delivery catheter 300 can include the shaft 304, and the shaft 304 may include one or more internal lumens therein. In the illustrated embodiment, for instance, the shaft 304 includes three lumens 310, 312, 314. Each lumen may be used to receive a different fluid and/or to fulfill a different purpose in the use of the delivery catheter 300. For instance, a primary lumen 310 may receive a cardioplegic fluid therein. A second lumen 312 may receive a fluid for inflating the expandable member 308, while a third lumen 314 may be used to monitor a pressure in a patient's vasculature, such as in the coronary sinus.

FIG. 4B illustrates more particularly an exemplary structure of the shaft 304 according to some embodiments. By way of illustration, in this embodiment, the shaft 304 may have a generally circular cross-sectional shape, which material may define the three lumens 310, 312, 314; however, in other embodiments the shaft 304 may instead have an elliptical, hexagonal, polygonal, or other regular or irregular cross-sectional shape. A single material may be used to form the shaft 304. In FIG. 4A, however, the shaft may include multiple materials that are combined together. For instance, an outer shell 305 may be used to primarily define the three lumens 310, 312, 314, although in other embodiments, an outer shell may singularly or collectively with other elements define a different number of lumens. For instance, in alternative embodiments, a single lumen may be formed in the exterior material 305. In such a case, if multiple lumens are desired, interior liners or other structures may be used to separate the single lumen into multiple compartments.

The outer shell 305 may be formed of any suitable material and using any number of different manufacturing processes. Suitable polymeric materials for the hollow liner 316 or coating 321 may include, for instance, ethylene tetrafluoro ethylene (ETFE) or polytetraflourothylene (PTFE). In another embodiment, the outer shell 305 is formed from a biocompatible material such as Pebax®. An outer shell 305 produced from Pebax® may, for instance, be extruded, and can even be extruded to define multiple lumens. As described in more detail hereafter, the outer shell 305 may, in some cases, have a variable durometer along its length. For instance, the durometer may be in a range between about 20 to about 80 Shore D, with different portions of the outer shell 305 having different durometer.

Further, as noted previously, the shaft 304 may be structured to be radiopaque so as to facilitate visualization by fluoroscopy, an angiogram, or other suitable visual technology. Echocardiography may also be used. To facilitate visualization and/or echogenicity, the outer shell 305 may include, in at least one embodiment, materials, markers, additives, or other elements that facilitate visualization by x-ray or ultrasound. By way of illustration, the outer shell 305 can include, in at least one embodiment, an additive such as barium sulfate. When the outer shell 305 is extruded or otherwise formed, the barium sulfate or other additive can be concentrated within the outer shell 305. A concentration between fifteen and thirty percent may, for instance, allow the shaft 304 to be highly visible during a fluoroscopic procedure.

The primary lumen 310 defined by the exterior material 305 may itself facilitate transfer of cardioplegic fluid or another fluid; however, in other embodiments the primary lumen 310 may facilitate other or additional aspects. For instance, in FIG. 4A, the primary lumen 310 includes multiple components therein. In particular, in FIG. 4A, the primary lumen 310 includes multiple layers in a laminate manner. The multiple layers may be separately or integrally combined.

One example of a component for use with the shaft 304 may be a hollow liner 316. The liner 316 may be sized to fit within the primary lumen 310 of the outer shell 305, and can have any number of purposes. In this embodiment, the liner 316 may be substantially impermeable. Consequently, a cardioplegic or other fluid may be passed from a fluid source and through the liner 316. The fluid may flow into the patient and to a desired location, or out of the patient. Where a fluid source is exterior to the patient, a desired location for the fluid may include the coronary sinus, and the cardioplegic fluid may be retrograde cardioplegia.

The liner 316 is optionally reinforced. For instance, the liner 316 may have a reinforcement structure 318 around or proximate at least a portion thereof. The reinforcement structure 318 can also be positioned within the primary lumen 310 defined by the exterior material 305 of the shaft 304. In FIG. 4A, the reinforcement member 318 takes the form of a braided shroud that extends around an exterior surface of the liner 316, although in other embodiments the reinforcement structure 318 can take any number of other desired forms. For instance, the reinforcement structure 318 may alternatively be a solid shroud, a set of longitudinal wires, or other component. Regardless of the type of structure, the reinforcement structure 318 may in some cases provide added stiffness to the shaft 304. By way of example, the reinforcement structure 318 may have a column stiffness of greater than that of the liner 316 and/or the outer shell 305, or which when added to the outer shell 305 and/or the liner 316, increases the column stiffness of the shaft 304. In some embodiments, the reinforcement structure may prevent or reduce the chance that as the shaft 304 flexes, the liner 316 and/or the primary lumen 310 is pinched closed to restrict fluid flow.

The reinforcement member 318 may further promote desired torsional or other characteristics of the shaft 304. For instance, the shaft 304 may be guided through a patient's vasculature to a desired position and, as described hereafter, may be articulated so as to facilitate passage into a particular vein, artery, or other body lumen. The shaft 304 may be articulated by, for instance, rotating the user interface 302. Due to the reinforcement member 318, the torque transmission through the shaft 304 may be improved as compared to a shaft made of a single polymer material. The shaft 304 may thus respond to desired torque while minimizing twisting of the shaft 304 beyond a torque applied. Moreover, as the tip of the shaft 304 is articulated—such as by using a switch or other mechanism as described herein—certain materials or components may tend to curl out of plane. In particular, as a tip is articulated, the shaft 304 may be held along an axis, and it is desired to articulate while remaining in-plane. Such a characteristic may be known as pig-tailing. When a device pig-tails, the tip may curve out of plane, like a pig-tail, resulting in the tip of the shaft 304 articulating and moving unpredictably and causing the surgeon to spend additional time attempting to fit the tip of the shaft 304 into a desired location. Alternatively, when the shaft 304 behaves predictably—such as by remaining in plane during articulation—the surgeon may reliably orient the shaft 304, and articulate the tip of the shaft 304 to pass into a desired lumen, without resorting to trial-and-error or other time consuming processes.

While the reinforcement member 318 may thus be desirable for column stiffness and/or torque-related purposes, in other embodiments the reinforcement structure 318 may be eliminated entirely, may be repositioned (e.g., to be external to the primary lumen 310), or otherwise configured. The reinforcement member 318 may also be formed of any suitable material. For instance, in one embodiment, the reinforcement member 318 is stainless steel, although the reinforcement member 318 may be formed of any other metal, alloy, composite, organic material, polymer, or other material, or any combination of the foregoing. Furthermore, in some embodiments, the reinforcement member 318 may additionally or alternatively facilitate visualization of the shaft 304. For instance, all or a portion of the reinforcement member 318 may be radiopaque or echogenic to promote higher visibility of the shaft 304. By way of illustration, where the reinforcement member 318 includes a metal, the shaft 304 may have higher echogenicity than a similar device comprising only a plastic material.

In at least one embodiment, the reinforcement member 318 may be integrally connected to one or more other components within the shaft 304. For instance, the outer shell 305 may be heated or compressed. Where the reinforcement member 318 has a braided construction, or another configuration in which openings are formed, the outer shell 305 may be at least partially melted such that the outer shell 305 melts into, and is bonded with, the braided reinforcement member 318.

Also within the primary lumen 310 of FIG. 4A is a pull-wire 320. As briefly noted above, the shaft 304 can in some embodiments be configured to be selectively moved, or articulated. Articulation of the shaft 304 can facilitate locating of the shaft 304, or a tip of the shaft 304, at a desired location as well as retraction of the shaft 304 when a procedure is complete. The pull-wire 320 may be used in some embodiments to facilitate such articulation of all or a portion of the shaft 304. For instance, a distal portion of the shaft 304 may be articulated to facilitate positioning of a distal tip 306 (FIG. 5A) of a shaft 304 into a coronary sinus or other desired location, and allow an occluding member (such as the expandable member 308 depicted in FIG. 5A) to fully or partially occlude the coronary sinus. Positioning of the distal tip 306 in such a manner may also allow monitoring of a pressure within the patient and/or delivery of a cardioplegic fluid into the coronary sinus.

In general, the pull-wire 320 may extend through all or a portion of the length of the shaft 304. In the illustrated embodiment, the pull-wire 320 is positioned within the primary lumen 310 of the shaft 304. The pull-wire 320 can extend to the distal tip 306 of the shaft 304. Consequently, as a longitudinally directed force is applied to the pull-wire 320, the pull-wire 320 potentially moves within the primary lumen 310, or otherwise allows the shaft 304 to articulate to accommodate the applied force.

The pull-wire 320 is illustrated in FIG. 4A as also being located within or in contact with the reinforcement member 318, and/or as having a jacket or coating 321 thereon. Such structure should, however, be understood to be merely exemplary. In other embodiments, for instance, the liner 316, exterior to the reinforcement member 318, or even in a lumen separate from the primary lumen 310. According to at least one aspect, the pull-wire 320 is placed within the reinforcement member 318 and/or within the coating 321 allowing the reinforcement member 318 and/or the coating 321 to act as a lumen allowing decreased friction movement for the pull-wire 320. In addition the liner 316 material could be a fluoropolymer (ETFE or PTFE) to provide for this decreased friction. It is desired that the pull-wire moves easily within the liner so the device responds quickly to the user input at the handle. The pull-wire 320 and/or coating 321 can be made of any number of materials, or have a variety of other characteristics. For instance, the pull-wire 320 may be stainless steel or another metal, alloy, composite, ceramic, polymer, or other material, or any combination thereof. Moreover, the pull-wire 320 may be expected to have longitudinal forces applied. The pull-wire 320 may have strength characteristics to largely reduce a risk of plastic deformation when expected forces are applied; however, in other embodiments the pull-wire 320 may be expected to plastically deform, and may be a ductile material that plastically deforms but with a reduced risk of fracture. While the pull-wire 320 of FIG. 4A is illustrated as having a generally rectangular cross-sectional shape, it should also be appreciated that the pull-wire 320 can be circular, elliptical, or have any other suitable shape.

With continued reference to FIGS. 3 and 4A, the various lumens within the shaft 304 may each be in fluid communication with one or more desired fluids. As shown in FIG. 3, for instance, such fluid communication may be facilitated by a hub 322 and/or a set of arms 324, 326, 328. More particularly, in this embodiment, a proximal end 330 of the shaft 304 is connected to a hub 322. The hub 322 may include multiple extensions, and each extension can be routed to one or more of the lumens within the shaft 304. For instance, in the illustrated embodiment, the hub 322 includes three extensions. A first extension 324 may extend from, or otherwise be connected to the hub 322. The first extension 324 may be used to, among other things, deliver cardioplegic fluid. In such an embodiment, a source of cardioplegic fluid may be connected to the first extension 324 and/or a stopcock 325 or other valve disposed on or connected to the first extension 324. A pump or other device may cause a fluid to flow at a desired rate and/or pressure, while the stopcock 325 can further restrict or isolate fluid flow through the first extension 324 and into the patient. As the fluid flows, the fluid may pass through the extension 324 and into a lumen (e.g., primary lumen 310 of FIG. 4A) of the shaft 304.

The second and third extensions 326, 328 may also be in communication with the second and third lumens 312, 314, respectively, of the shaft 304 as shown in FIG. 4A. The second extension 326 may be configured to receive a liquid or gas directed to the expandable member 308 at the distal end of the shaft 304. Consequently, the second extension 326 and/or a stopcock 327 or other valve thereon, may be connected to an inflation device (not shown). The inflation device may be used to force a fluid into the second lumen 312. At the distal end of the shaft 304, the second lumen 312 may be in fluid communication with the expandable member 308, which can be a balloon. The fluid may flow through the second lumen 312 and into the balloon, which is caused to inflate. The balloon can inflate fully or partially, and can fully or partially occlude a lumen such as a coronary sinus of a patient. In other embodiments, the expandable member 308 may be something other than a balloon. For instance, the expandable member 308 may include a mechanically expanding mechanism. In such a mechanism, a series of flexible beams may be mounted longitudinally and be deflected outward by exerting a compressive force on the beams using a pull wire or other mechanism. A substantially impermeable membrane may be mounted to the beams to provide sufficient occlusion properties.

Where the expandable member 308 is a balloon or other similar device, the degree of occlusion may be controlled by, among other things, the amount of fluid passed through the second lumen 312 and into the expandable member 308. For instance, in one embodiment between one and three cubic centimeters of fluid may be used to inflate a balloon or other suitable expandable member 308. In some embodiments, the stopcock 327 may include, or have attached thereto, a pressure relief valve to reduce the risk that overinflation of the expandable member 308. For instance, the pressure relief valve may open and receive fluid from the second lumen 312 when the expandable member 308 exceeds a maximum desired size, and pressure builds within the expandable member 308.

It should be appreciated by one skilled in the art in view of the disclosure herein that the degree of occlusion may be varied based on various factors. For instance, where the expandable member 308 is within a coronary sinus, it may be desirable that only partial occlusion occur. More particularly, the coronary sinus may be rather fragile. Accordingly, if the expandable member 308 is over inflated, the expandable member may cause the coronary sinus wall to rupture or tear, thereby necessitating emergency corrective procedures. To guard against such an outcome, the expandable member 308 may be only partially inflated so as to not exert a large force on the interior surfaces of the coronary sinus. Such use may result in partial occlusion where fluid is able to pass around the expandable member 308. Further, because the expandable member 308 may not grip tightly against the coronary sinus or other body lumen, the expandable member 308 may be able to dynamically move within the coronary sinus or other lumen. Such movement may not be problematic or, if undesired, may be counteracted by the shaft 304 of the present invention, which can have sufficient column stiffness to effectively stabilize the position of the expandable member 308 without securing the expandable member 308 directly to the lumen wall.

The third extension 328 may connect to a pressure monitoring system (not shown) or other device, and may do so directly or through a stopcock 329 or other valve. For instance, in one embodiment, the third extension 328 may facilitate measuring or other monitoring of a pressure within the coronary sinus or other body lumen of a patient. For instance, the third lumen 314 (FIG. 4A) may extend through the shaft 304 and terminate at or near the distal tip 306. At or near the distal tip 306, the third lumen 314 may be opened so as to be in fluid communication with a fluid outside the shaft. Based on the location of the termination of the third lumen 314, a pressure monitoring system may measure pressure on the proximal or distal side of the balloon or other expandable member 308. Where the expandable member 308 is within the coronary sinus, the pressure monitoring system may therefore obtain fluid from the site, or pass fluid into the site, in a manner that measures the coronary sinus pressure. The stopcock 329 may also include or be attached to a pressure relief valve similar to that described above with respect to stopcock 327. If the cardioplegic fluid pressure exceeds a predetermined level (e.g., 40-50 mm Hg of mercury), the pressure relief valve can open and release the fluid pressure. By releasing the fluid at or above a predetermined pressure, the occurrence of hemolysis in a blood component of cardioplegic fluid can be avoided, or the coronary sinus can be protected from excessive pressure and possible rupture or other damage.

The shaft 304 of the delivery device 300 can have a length sufficient for locating the expandable member 308 and/or the distal tip 306 in desired locations. In locating the expandable member 308 and/or the distal tip 306, the user interface 302 can remain at least partially outside of the patient, and can be manipulated by a surgeon or other operator. In one embodiment, the shaft 304 may be at least about fifty centimeters long. In other embodiments, the shaft 304 may be at least about sixty centimeters long, as measured from the distal tip 306 to the proximal end 330 of the shaft 304. In still other embodiments, the shaft 304 may be longer than about sixty centimeters or shorter than about fifty centimeters.

Figure 5A:
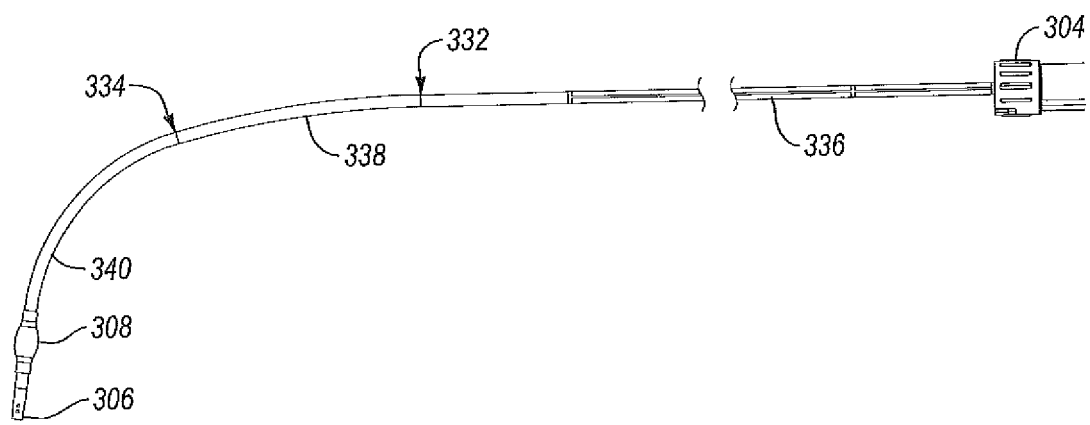
FIG. 5A is a side view of the catheter shaft of FIG. 3, the catheter shaft being articulated at the distal end thereof.
Figure 5B:
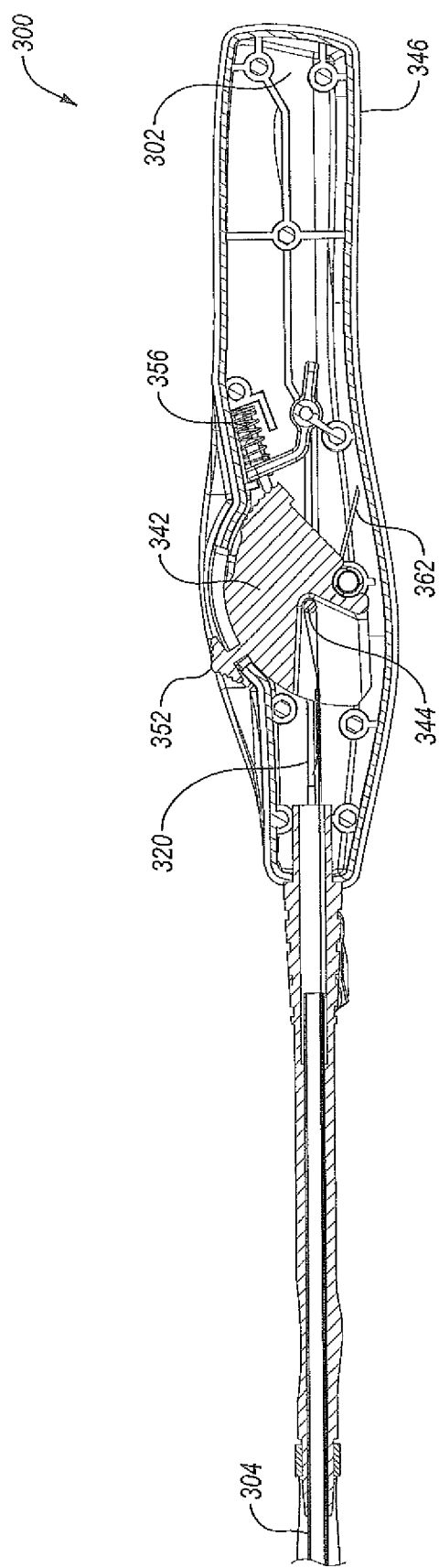
FIG. 5B is a partial cross-sectional side view of a user interface and proximal end of a shaft of the retrograde cardioplegia delivery catheter of FIG. 3.

With continued reference to FIGS. 5A and 5B, and as noted previously above, a pull-wire 320 may extend through, or otherwise be associated with, the shaft 304. The pull-wire 320 or another suitable mechanism may be used to selectively articulate at least the distal portion of the shaft 304. For instance, by pulling the wire 320, a user may cause at least the distal end of the shaft 304 to bend or flex in a desired manner. As discussed above, flexure of the distal end of the shaft 304 may allow a surgeon to efficiently locate the expandable member 308 and/or the tip 306 at a desired location within a patient.

FIG. 5A illustrates an exemplary embodiment of the shaft 304 when articulated. In particular, the position of the shaft 304 may be an articulated position, and may particularly correspond to a position or orientation of the distal tip 306 when a longitudinal force is applied to a pull-wire 320 or other mechanism. The particular amount by which the distal tip 306 moves and/or the shaft 304 flexes can vary based on any of various considerations. For instance, the amount of displacement of the pull-wire may determine the extent of movement by the distal tip 306. Moreover, the stiffness of the shaft 304 may also define the degree to which the shaft 304 moves, flexes, or bends with an applied force.

In one embodiment, the shaft 304 may be at least partially flexible, and in still other embodiments may be a multiple durometer shaft. As discussed above, the durometer of the shaft 304 may vary along its length. Consequently, the hardness of the shaft 304 may vary from one location to the next. By way of illustration, the shaft 304 of FIG. 5A is illustrated as having three segments, each of which has a different durometer. As the shaft 304 flexes, the extent of flexure may vary in any or all of the three segments. Locations where durometer changes or transitions occur may define inflection points at which a degree or extent of flexure changes.

As shown in FIG. 5A, for instance, the exemplary shaft 304 has two inflection points 332, 334. More particularly, three segments 336, 338, 340 can be formed, and the first inflection point 332 may be located about at a location where the durometer changes between the first and second segments 336, 338. The second inflection point 334 may be located about at a location where the durometer changes between the second and third segments 338, 340 of the shaft 304. As a pull-wire is pulled, or another mechanism used, one or more of the three segments 336, 338, 340 may flex and deflect. The third segment 340 of FIG. 5A is shown as having the largest deflection, while the first segment 336 may have the least deflection.

As noted above, the degree of flexure or deflection of the three segments 336, 338, 340 may vary. In one example embodiment, for instance, the third segment 340 may bend to have a curve radius of between about five and about eight centimeters and/or deflection at the distal end of the third segment 340 may be between about eighty-five and about ninety-five degrees. For instance, the curve radius of the third segment 340 may be about 6.4 centimeters, and deflection from horizontal about eighty-nine degrees (e.g., along a longitudinal axis of the first segment 336). The second segment 338 may bend to have a curve radius between about 2.5 centimeters and about 3.5 centimeters and/or deflection at the distal end of the third segment may be between about ten and about twenty degrees relative to the longitudinal axis of the first segment 336. For instance, the curve radius of the second segment 338 may be between eighteen and about forty centimeters. For instance, the curve radius of the second segment 338 may be about twenty-nine centimeters and/or the deflection from horizontal about fifteen degrees. The first segment 336 may be flexible and bend; however, the first segment 336 may have a bend radius much larger than the second segment 336, or may be relatively unaffected by a force applied to a pull-wire or other mechanism. In some embodiments, the bend radius of the first segment 336 varies along its length while the bend radii of the second and third segments 338, 340 are generally constant along the respective lengths thereof. In other embodiments, the bend radii of the second and/or third segments 338, 339 may vary along their lengths, such as where bending follows an elliptical path.

The illustrated embodiment is merely one example of the manner in which the shaft 304 may bend, flex, or deflect. In some embodiments, flexure of any or all of the segments 336, 338, 340 may be lesser or greater than the exemplary values given. For instance, in one embodiment, the illustrated curvature is exemplary of an engagement position in which the shaft 304 generally follows a contour which approximates the curvature of the vasculature of the patient, and/or which facilitates locating the expandable member 308 within the coronary sinus of a patient. The vasculature of any particular patient, including the direction of the coronary sinus. Consequently, the ideal articulation of the shaft 304 may vary from patient-to-patient. For instance, if less curvature is needed or desired, the force on pull-wire or other mechanism may be decreased, whereas if a greater curvature or flexure is desired, the force on the pull-wire or other mechanism may be increased.

The force on the pull-wire or other articulation mechanism may be only one factor that determines the degree of bending in the shaft 304. For instance, the durometer and/or length of each of the various segments may affect the degree of articulation or deflection of a particular segment of the shaft 304. By way of illustration, an exemplary shaft 304 may be approximately 58 centimeters long, as measured between the hub 322 and the distal tip 306. The first segment 336 may be approximately 42.5 centimeters in length, and have a durometer of approximately 72 Shore D. The second segment 338 may be approximately 7.5 centimeters in length and have a durometer of approximately 55 Shore D. The third segment 340 may be approximately 8 centimeters long and have a durometer of about 40 Shore D. In some embodiments, the distal tip 306 may be atraumatic. For instance, the distal tip 306 may have a durometer of approximately 25 Shore D so as to be sufficiently soft to reduce a risk of trauma to the coronary sinus or other location within a patient. The example lengths and durometer values above are merely exemplary. For instance, the durometer and/or length of any or all of the segments 336, 338, 340 may be increased or decreased, and such changes may affect the degree of deflection, the radius of curvature, or otherwise affect the manner in which a particular segment bends, flexes, or otherwise articulates.

In accordance with one example embodiment, the articulation of the shaft 304 is selectively controlled by a surgeon or other operator of the retrograde cardioplegia delivery catheter 300. For example, with reference again to FIG. 3, a user interface 302 may be a handle used by the surgeon or clinician to selectively control articulation of the shaft 304. More particularly, in some embodiments a multi-position switch body 342 may be used in this example embodiment to control articulation of the shaft 304, including the distal tip 306.

Figure 5C:
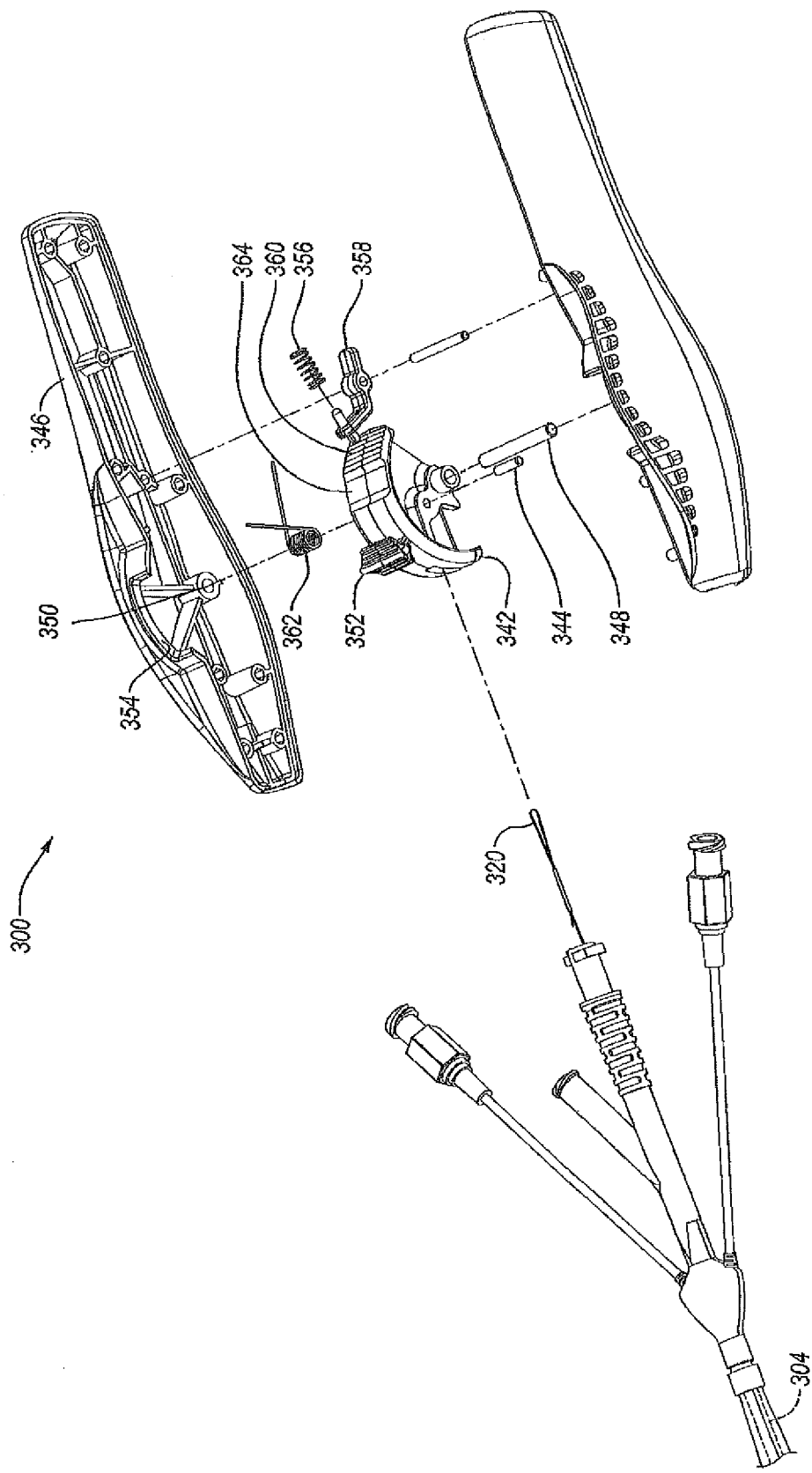
FIG. 5C is a partial cross-sectional, exploded assembly view drawing of the user interface and shaft of FIG. 5B.

FIGS. 5B and 5C illustrate partial cutaway views of the illustrated user interface 302 in greater detail. As described herein, the user interface 302 can selectively articulate the shaft 304, possibly between any number of discrete shapes, positions, or other configurations. More particularly, the user interface 302 of FIGS. 5B and 5C may be used to articulate the shaft 304 potentially in both discrete increments, and infinitely small increments.

The user interface 302 of the present embodiment may be a handle or grip portion which a surgeon, clinician, or other operator of the retrograde cardioplegia delivery catheter 300 can grasp. Using the grip, the operator can direct the distal tip 306 (FIG. 3) of the delivery catheter 300 through the patient, or fully or partially retract the delivery catheter 300. The user interface 304 may also include the multi-position switch body 342 that may be used to change the shape or other configuration of the shaft 304.

To articulate the shaft 304 in a desired manner, a pull-wire 320 of the shaft 304 may be attached to the switch body 342. For instance, as best illustrated in FIG. 5C, the switch body 342 may include a pin 344 attached thereto. The pin 344 may, for instance, be placed within a recess of the switch body 342; however, a pin 344 or other attachment mechanism may be otherwise constructed. For instance, the pin 344 may alternatively be integrally formed with the switch body 342. By virtue of the pin 344 being securely connected to the switch body 342 and a proximal end of the pull-wire 320, as the switch translates, rotates, or otherwise moves, the pin 344 may also move. Where the pull-wire 320 is connected to the pin 344, the proximal end of the pull-wire 320 may therefore also be moved a distance corresponding to the distance of movement undergone by the pin 344. Movement of the pull-wire 320 may place a force on the pull-wire 320, which force may be directed generally along a longitudinal length of the pull-wire 320.

The switch body 342 may be mounted within a housing 346. For instance, the housing may define a recess or opening into which a switch pin 348 is located. A corresponding recess or aperture 350 may be formed at least partially through the switch body 342. The switch pin 348 may be journaled or otherwise secured within the aperture 350 in a manner that allows the switch body 342 to rotate around the switch pin 348. The switch pin 346 can thus act as a pivot point about which the switch body 342 rotates.

The switch body 342 includes, in the embodiment shown in FIGS. 5B and 5C, a switch 352 which the user may use to rotate or otherwise move the switch body 342. For instance, the user may place a thumb or finger on the switch 352 and apply a downward and/or lateral force that causes the switch 352 to translate within a recess 354 formed in the housing 346. As the switch body 342 rotates, the pin 344 that is mounted within the switch body 342 can also move at least partially around, or relative to, the switch pin 348. The pull-wire 320, which is attached to the pin 344, may also move as a result of a force placed thereon.

In some embodiments, the travel distance of the switch 352 may correspond generally to the travel for the pull-wire 320. For instance, the switch 352 and pull-wire 320 may move such that a one-to-one correspondence exists between movement of the switch 352 and the distal tip of the shaft 304. By way of illustration, moving the switch 352 a distance of one-half inch may also move the pull-wire 320 about one-half inch. In other embodiments, however, there may be a ratio applied between the travel distance of the switch 352 and the pull-wire 320. For instance, to change the sensitivity of the articulating tip of the shaft 304, the pull-wire 320 may be geared up or down relative to the switch 352. By way of illustration, in FIGS. 5B and 5C, the switch 352 rotates around the switch pin 348, and has an arcuate travel path. The pin 344 can also rotate around an arcuate path around the switch pin 348. The radius from the switch pin 348 to the pin 344 may, however, be different than the radius from the switch pin 348 to the switch 352. As the travel distance is an arc length which is based on the radius of rotation, the switch 352 within the recess 354 may travel a first distance, and the pin 344, and thus the pull-wire 320, can move a lesser amount. In this or another similar manner, the sensitivity and/or control of the device 300 may be modified. More particularly, in this embodiment, better control may be obtained by allowing the switch 352 to be moved less finely. In other embodiments, the movement of the pull-wire 320 and switch 352 can be related in other manners. For instance, a cam surface, roller, or other mechanism may be used to adjust the motion of the pull-wire 320 relative to the switch 352.

As further shown in FIGS. 5B and 5C, the housing 346 of the user interface 302 optionally includes a biasing member 356 positioned therein. In this embodiment, the biasing member 356 is a spring and may be secured within a chamber of the housing 346, although any suitable biasing member or mechanism may be used. The spring or other biasing member 356 may engage a pawl 358, and be configured to exert a biasing force thereon. The pawl 358 may, in turn engage the switch body 342.

In the illustrated embodiment, the switch body 342 has a proximal exterior surface that defines multiple ridges 360 that can be engaged by the pawl 358. For instance, a set of ridges 360 may have grooves therebetween. As the surgeon or other operator moves the switch 342, operator can overcome the biasing force of the biasing member 356. As a result, the pawl 358 may move over the ridges 360 and settle into grooves therebetween. Due to the biasing force exerted by the biasing member 356, the pawl 358 may click into each groove on the switch body 342.

The ridges 360 may also counteract the biasing force to at least some degree. For instance, if an operator releases the switch 352 while the pawl 358 is within a groove between ridges 360, the ridges 360 may cause the pawl 358 to remain substantially stationary. Indeed, the ridges 360 may also counteract additional biasing forces in some embodiments. For instance, as shown in FIGS. 5B and 5C, a second biasing member 362 may act upon the switch body 342. The second biasing member 362 may, for instance, be a torsion spring. In one embodiment, the second biasing member 362 exerts a biasing force on the switch body 342, which biasing force tends to push or otherwise move the switch 352 to the position illustrated in FIG. 5B. At such a position, the pawl 358 may be located adjacent a proximal-most one of the ridges 360. However, as noted previously, the ridges 360 may also counteract the biasing force of the second biasing member 362. More particularly, if an operator releases the switch 352 while the pawl 358 is between ridges 360, the ridges 360 may counteract the biasing force and tend to maintain the switch body 342 at the position when released, without reverting back to the initial position illustrated in FIG. 5B.

In this manner, the user interface 302 may provide multiple different, discrete positions at which the pull-wire 320 can be located, even in the absence of the application of continued force by the operator to the switch 352. The particularly number of discrete positions may vary. For instance, there may be a single discrete position, or up to between three and fifteen positions, such as may occur if there are up to fifteen ridges 360. Each discrete position may correspond to a discrete position of the pin 344, and thus also the pull-wire 320 and the distal tip of the shaft 304. In other embodiments, more or fewer discrete positions may be included, or no discrete positions may be provided.

As further shown in FIG. 5C, the switch body 342 of the illustrated embodiment may also include a region in which there are no ridges. More particularly, a smooth region 364 is provided on a periphery of the switch body 342, and the pawl 358 may move over such region. If the operator releases the switch 352 while the pawl 358 is being advanced along the smooth region 364, there may be a lack of structures for the pawl 358 to engage. As a result, the second biasing member 362 may cause the switch body 342 to rotate and retreat. In some embodiments, the switch body 342 may retreat to a position at which the pawl 358 again engages against one of the ridges 360.

As will be appreciated in view of the disclosure herein, while the operator moves the switch 352 such that the pawl 358 engages the smooth region 364 rather than the ridges 360, the pin 344 and pull-wire 320 may continue to move. However, such elements may effectively slide between positions, which results in movement in very small, if not infinitely small, increments. In some aspects, to maintain the pull-wire 320, and thus the distal tip of the shaft 304 at a corresponding position, the operator may maintain pressure on the switch 352. Without such pressure, the switch 352 may revert to an intermediate state. Such reversion may be desirable in some aspects. For instance, a troubleshooting position may be desirable while attempting to locate the distal tip 306 in the coronary sinus. However, when retracting the shaft 304 from the patient, a position of the distal tip 306 that is fully articulated, or which otherwise is articulated beyond the intermediate, engagement position, may have a higher likelihood of damaging the coronary sinus. Thus, automatic retraction of the distal tip 306 to the engagement position, upon release of the switch 352, can decrease a potential for operator error with the catheter 300.

In some embodiments, an automatic retraction of the articulated distal tip 306 may not be provided, or may be combined with other features. For instance, a tactile response may be provided so as to alert the surgeon or other operator as to the position of the distal tip 306. In one embodiment, for instance, a cam may be included. To articulate the distal tip 306, the cam may rotate and, at a point, my push or move an element that presses against the hand of the operator. As a result, the operator can be alerted as to whether the desired position is being exceeded, and helping to alert operators that they may be overshooting a desired position of the distal tip 306.

Figure 6A:
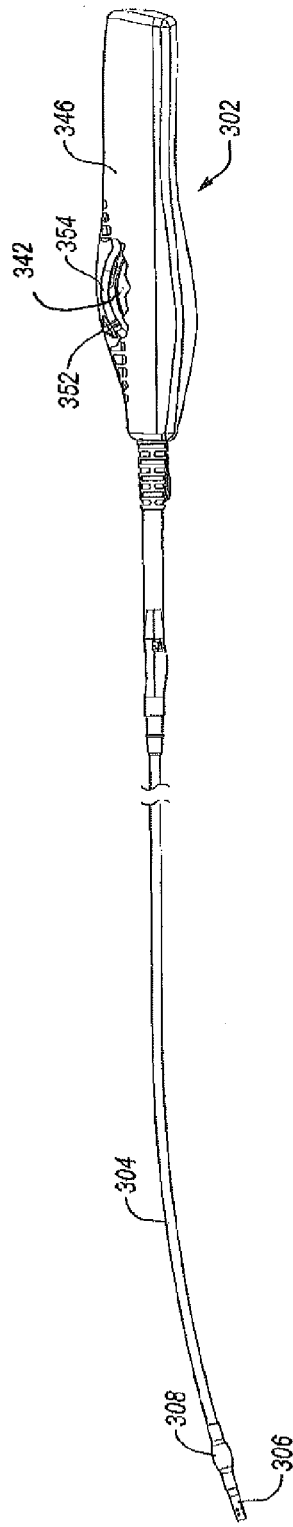
FIGS. 6A-6C illustrate partial views of the retrograde cardioplegia delivery catheter of FIG. 3, with a switch at various positions and distal tips of the catheter shaft having corresponding articulated positions.
Figure 6B:
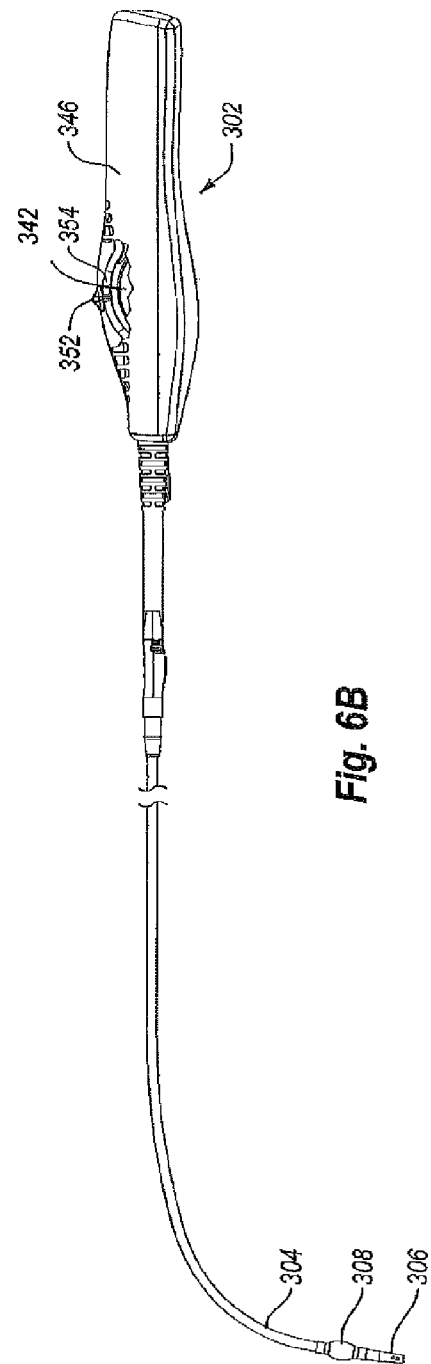
Figure 6C:
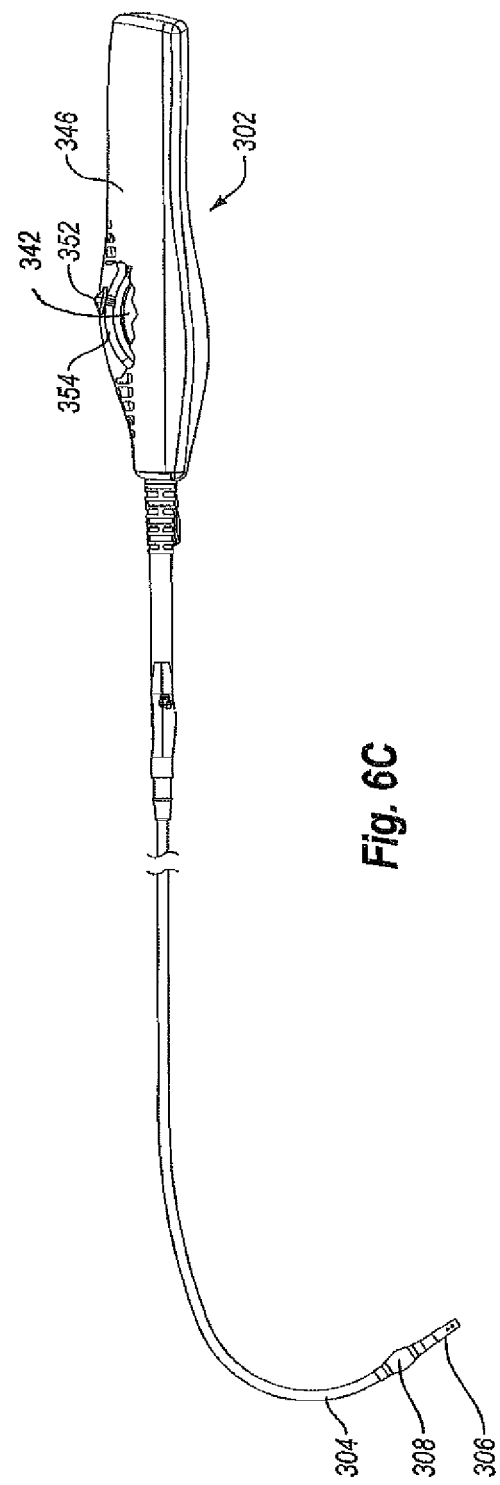

FIGS. 6A-6C illustrate exemplary embodiments in which the switch body 342 is positioned at various locations within the recess 354 of the housing 346, along with a corresponding configuration of a distal tip 306 of the shaft 304 at each such position of the switch body 342. In some embodiments, the configurations of the distal tip 306 may be curved, and can be at pre-set curves configured to provide certain features. For instance, different curves may generally facilitate insertion of the shaft 304 into a patient, locating of the distal tip 306 in the coronary sinus of a typical patient, and/or troubleshooting a process of locating the distal tip 306 in the coronary sinus of a patient having a coronary sinus configuration deviating from an average configuration.

In general, FIG. 6A may correspond to an initial position of the switch 352, and may correspond generally to the position of the switch 352 illustrated in FIG. 5B. FIG. 6B may correspond to an intermediate return position of the switch 352 when released, and when the pawl 358 of FIGS. 5B and 5C had passed onto the smooth region 364. FIG. 6C may correspond to an extended position at which the switch 352 is fully rotated and/or at which the distal tip 306 is fully articulated.

More particularly, and with reference to FIG. 6B, the pawl 358 (FIG. 5C) may engage a distal-most ridge 360 before the smooth region 364. In such position, the pawl 358 may be moved partially along the recess 354 in the housing 346. This intermediate position may be referred to as an engagement position. Generally speaking, the engagement position of the switch body 342 and switch 352 may correspond to a particular position of the shaft 304 and distal tip 306, in which the curvature of the shaft 304 is intended to approximate a typical curvature to be expected in the average patient, so as to position the distal tip 306 of the shaft 306 within the patient's coronary sinus. To reach the engagement position, the distal tip 306 may deflect between about eighty-five to about ninety-five degrees from horizontal. In some embodiments, the engagement position corresponds to the position of the shaft 304 and distal tip 306 of FIG. 5C.

An initial position of the switch body 342 and switch 352 (e.g., when the pawl 358 of FIG. 5C is at a first ridge 360) and/or where the switch 352 is at a distal end of the recess 354 as shown in FIG. 6A, may be considered in some embodiments to be an insertion position. The insertion position may be configured for use where, for instance, the surgeon or other operator is inserting the shaft 304 into the patient. As noted above, one or more discrete positions optionally exist between the insertion and engagement positions. Such positions may be used during insertion of the shaft 304 into a patient and/or during locating of the distal tip 306 into a desired location within the patient. At the insertion position, the shaft 304 may have a substantially straight configuration. Alternatively, as shown in FIG. 6A, when the device 300 is in the insertion position, the distal end of the shaft 304 may have predetermined flexure or deflection. Such a curvature may be used to, among other things, facilitate insertion of the shaft 304 into an introducer sheath or other component, as well as into the patient. The amount of predetermined flexure may also vary, for instance, while at the insertion position, the distal tip 306 of the shaft may have a deflection angle between about five and about twenty-five degrees; however, the deflection angle may be greater or lesser in other embodiments.

In another aspect, the curvature may provide a visual manner in which a surgeon can use the user interface and identify the plane in which the distal tip 306 will bend when placed within a patient. A line may also be printed or otherwise provided along an exterior surface of the shaft 304 to provide a visual indication of the orientation and/or flexure direction of the distal tip 306. Additionally, or alternatively, the housing 354 may facilitate determining the flexure plane. For instance, the housing 354 may be asymmetrical, with an asymmetrical or other element aligned with the flexure plane.

If the switch 352 is allowed to travel past the engagement position, the switch 352 and the shaft 304 can enter into a troubleshooting position. FIG. 6C illustrates a troubleshooting position where the switch 352 is positioned at the proximal end of the recess 354, and may correspond to a maximum articulation, flexure, or deflection of the distal tip 306 of the shaft 304. Generally speaking, if the surgeon is unable to place a distal tip 306 within a desired location of the patient using the engagement position, insertion position, or any positions therebetween, it may be that additional deflection at the distal tip 306 is desired so as to match the position of the coronary sinus or other lumen of the patient. The surgeon may thus move the switch 352 and the distal tip 306 of the shaft 304 into a troubleshooting position. Certain patients may, for instance, have a curvature to their vasculature that requires or benefits from a tighter curve than that provided at the engagement position. At the illustrated troubleshooting position, the distal tip may bend up to about ninety to about one-hundred fifteen degrees, or even more. In other embodiments, the shaft may be provided with less or more deflection. As noted previously, the troubleshooting position may be used by the surgeon; however, if the switch 352 is released, the switch 352 and the distal tip 306 may revert automatically back to the engagement position described previously.

FIGS. 6A-6C generally illustrate various positions of the user interface 302 and the distal tip 306 that may be used to locate the distal tip 306 of the shaft 304 at a desired position within a patient's body. Insertion of the distal tip 306 at the desired location may be important to, for instance, position an occluding member, supply cardioplegic fluid, or for any number of other reasons.

Figure 7:
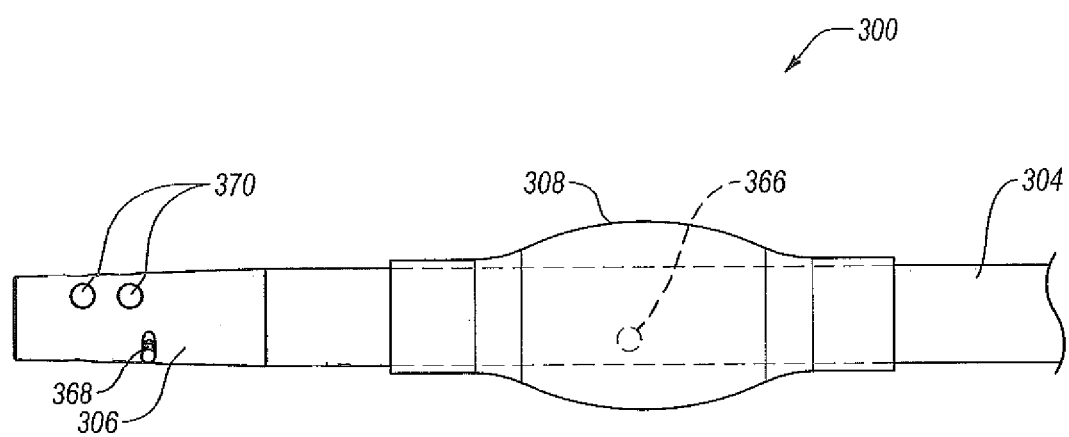
FIG. 7 illustrates a side view of a distal end of the retrograde cardioplegia delivery catheter of FIG. 3, the distal end including an expandable member and an atraumatic tip.

In one embodiment, such as that illustrated in FIG. 7, the shaft 304 of the delivery catheter 300 is provided with an expandable member 308 that may be used to, among other things, partially or fully occlude a coronary sinus or other lumen within the body of a patient. In the illustrated embodiment, the expandable member 308 is shown in an expanded state in which a width or diameter of the expandable member is increased; however, it will be appreciated that the expandable member 308 may also be retracted to a position at which the diameter or width is reduced.

The expandable member may include a balloon in some embodiments. For instance, the balloon may be inflated to occlude the coronary sinus. Exemplary balloons may be formed from a polyurethane or other material, and can be formed using a dip molding technique in which a mandrel is dipped in liquefied polyurethane or another material, and then cured. The expandable member 308 may then be attached to the shaft 304 by heat welding or another technique. Other techniques may also be used to produce the expandable member 308. For instance, the expandable member 308 may be formed of a pellethane material and blow molded, or may be manufactured using other techniques or materials.

The particular structure, shape, and configuration of the balloon or other expandable member 308 may be varied based on various factors, including the location of the lumen being occluded, the age, size, gender, or other characteristic of the patient, or other factors or any combination of the foregoing. For instance, in some embodiments, the shape of the expandable member 308 may be generally spherical. In other embodiments, however, the expandable member 308 may have an elongated structure. An elongated structure may, in some embodiments, provide additional length that can increase the stability of the distal end of the shaft 304 within the coronary sinus or other lumen of the user.

In accordance with one embodiment, the expandable member 308 may include a double-walled balloon having a maximum inflated diameter of up to about 17 mm, an uninflated diameter of less than about 6 mm, and a working length of about 10.5 mm. The expandable member 308 may be positioned about 15 mm from the distal tip 306 of the shaft 304. The length of the distal tip 306 is added so that the distance between the distal tip 306 and the expandable member 308 may facilitate positioning such that if the expandable member 308 is inadvertently or intentionally pulled from the coronary sinus, there may still be sufficient length of the shaft 304 distal to the expandable member 308 to eliminate a need to re-locate the shaft 304 within the coronary sinus. Accordingly, in some embodiments, the distal tip 306 extends distally relative to the expandable member 308, which may further facilitate engaging the ostia and advancing of the catheter 300.

As further shown in FIG. 7, the expandable member 308 may be secured to the shaft 304, and may be positioned concentric relative to the shaft 304. In at least one embodiment, the concentricity of the shaft 304 and the expandable member 308 may generally be maintained even during placement of the expandable member and occlusion of a body lumen. For instance, a traditional balloon catheter within the coronary artery may experience up to about forty percent eccentricity as the shaft shifts position within the center of the balloon. In contrast, embodiments according to the present disclosure may significantly reduce the ability and/or tendency of the shaft 304 to become eccentric during placement of the expandable member 308. For instance, in some embodiments, the illustrated embodiments may reduce eccentricity to approximately nine percent. Thus, eccentricity can be reduced by about 77% in accordance with embodiments of a retrograde cardioplegia delivery catheter 300 of the present disclosure.

Maintaining the shaft 304 concentric with the expandable member 308 may be desired for any number of reasons. For instance, as discussed herein, cardioplegic fluid or another fluid may flow from the shaft 304. If the shaft 304 is allowed to position itself eccentrically relative to the expandable member 308, the shaft 304 and/or the distal tip 306 of the shaft 304 may be positioned against a sidewall of a body lumen in which the expandable member 308 is located. As discussed herein, the coronary sinus may be relatively fragile when compared to other body lumens. If the fluid flows out of an eccentric tip, the fluid may flow directly into the sidewall of the coronary artery, thereby increasing a risk of injury or damage to the patient. By maintaining the shaft 304 concentric with the expandable member 308, there is an increased distance between the coronary artery sidewall and the opening where fluid escapes the shaft 304. Over such distance, the pressure may be relieved and the fluid dispersed so as to reduce the risk of injury to the patient.

As noted previously, the shaft 304 may include one or more lumens therein. For instance, as described relative to FIG. 3, three or more lumens may extend at least partially through a length of the shaft 304. As shown in FIG. 7, in at least one embodiment, an opening 366 is formed in the shaft 304. The opening 366 is illustrated as being within the expandable member 308. For instance, in some embodiments one of one or more lumens within the shaft 304 may include an inflation lumen. The inflation lumen may be in communication with the interior of the expandable member 308 through the opening 366. The opening 366 may be configured to allow delivery of an inflation fluid at a rate sufficient to inflate or otherwise expand the expandable member 308. For instance, the opening 366 may allow approximately two cubic centimeters of fluid to expand the expandable member 308 within about two seconds, although in other embodiments more or less fluid, or a longer or shorter inflation time may be provided, such that the flow rate and pressure can be varied. By way of illustration, the pressure within the expandable member 308 may be on the range of about 0.5 to about 2.0 pounds per square inch pressure. Furthermore, while only a single opening 366 is illustrated, in other embodiments, more than one opening 366 may be provided. Further still, the opening 366 may be positioned at any position within the expandable member 308 and need not be centered therein. In still another embodiment, the expandable member 308 may be self inflating and may, for instance, use cardioplegic fluid to inflate the expandable member 308.

A lumen used to inflate or expand the expandable member 308 is merely one example of a lumen that may be used in connection with the catheter 300. For instance, as described above, the illustrated catheter 300 may be suitable for use in occluding a portion of the coronary sinus, such as during a heart valve replacement or other procedure. For such a procedure, a fluid containing a cardioplegic agent such as potassium chloride may be directed through a lumen in the shaft 304 and discharged through one or more openings 370 and into the coronary sinus. The openings 370 may be in communication with a cardioplegic fluid delivery lumen. The primary lumen 310 in FIG. 4A is one example of a suitable lumen for delivering cardioplegic fluid. For instance, cardioplegic fluid may flow through an optional liner 316 (FIG. 4A) within the primary lumen 310. The liner 316 may end, or openings therein may be aligned with openings 370 near the distal tip 306 of the shaft 304. The fluid within the liner 316 may then pass through the openings 370 in the walls of the shaft 304, and into the coronary sinus 212. Cardioplegic fluid can be delivered through the catheter 300 and into the coronary sinus 212 at a sufficient pressure and volumetric flow rate (e.g., at about 200 cc/min at about 40 mm Hg) that the cardioplegic fluid will pass through coronary veins, crossing the capillary beds to the coronary arteries, and out the ostia.

A pressure lumen may also be provided within the shaft 304. The pressure lumen may also open to the environment on the exterior of the shaft and, in FIG. 7, may open at pressure ports 368 through a side wall of the distal tip 306 on the shaft 304. Alternately, a channel in the distal tip 306 could connect with the lumen used for pressure monitoring. At the illustrated position, the pressure ports 368 are distal to the expandable member 308. In such a position, upon locating the expandable member 308 within the coronary sinus of a patient, pressure within the coronary sinus and distal to the expandable member 308 may be monitored during cardioplegic fluid delivery. Monitoring the pressure in this manner can ensure that the pressure within the coronary sinus is maintained at a safe level so as to avoid causing a rupture or other damage to occur within in the coronary sinus. As discussed herein, the distal tip 306 may further be configured to reduce a likelihood of damage to the coronary sinus. For instance the distal tip 306 may be an atraumatic tip. More particularly, the distal tip 306 may have a low hardness (e.g., at or below 30 Shore D hardness), and may further be rounded or otherwise configured such that even in the event the distal tip 306 engages the coronary sinus, there is a low likelihood of damage.

It should be appreciated by one skilled in the art in view of the disclosure herein that the openings 370 and pressure ports 368 may be formed in the shaft 304 and/or distal tip 306 in any suitable manner. For instance, in at least one embodiment, the openings 370 and pressure ports 368 may be drilled into or otherwise formed in the shaft 304 following manufacture of the shaft 304 and/or tip 306. By way of illustration, in one embodiment, the tip 306 may be formed separately from the shaft 304, such as by using an insert mold. The tip 306 may thereafter be secured to the shaft using a thermal bonding process, an adhesive, or in another suitable manner. Following attachment of the tip 306 to the shaft 304, a drilling process may be performed to form the pressure ports 368 and attach such ports 368 to a pressure monitoring lumen within the shaft 304. In other embodiments, the tip 306 may be molded or otherwise formed such that the pressure ports 368 are pre-formed, and then are aligned with a pressure monitoring lumen of the shaft 304 during attachment of the tip 306 to the shaft. In other embodiments, the openings 370 through which cardioplegia flow and/or the pressure ports 368 may be placed in alternative locations. For instance, the pressure ports 368 may be formed on the shaft 304 rather than the distal tip 306, while the openings 370 may, in some embodiments, be on the distal tip 306. In some embodiments, the openings 370 and/or pressure ports 368 are formed by drilling or otherwise boring into the shaft 304.

Returning briefly to FIG. 3, it will be appreciated that in some embodiments, a retrograde cardioplegia delivery catheter 300 may include an anchor device 372. According to some embodiments of the present disclosure, the anchor device 372 may be movable relative to the shaft 304 and/or may connect to a contamination shield 374. In embodiments in which the anchor device 372 is moveable relative to the shaft 304, the contamination shield 374 may also slide or otherwise move relative to the shaft 304.

More particularly, as described above, a retrograde cardioplegia delivery catheter may be introduced into a patient's venous system through the right internal jugular vein, and advanced from there into the coronary sinus. To facilitate insertion of the delivery catheter, an introducer sheath may be used. In general, an introducer sheath may provide a smooth transition into the jugular vein so as to facilitate ease of entry of the delivery catheter with lowered insertion force. Additionally, an introducer sheath may provide lubricity to enhance pushability and passage of the catheter therethrough. The introducer sheath may remain in place at the patient's jugular throughout a procedure. In some embodiments, the exterior shaft 304 of the catheter 300 may be exposed to contaminants. Such contaminants may be on a surgeon or other clinician's hands, may be on a tray on which the catheter 300 is located, or may present in other locations.

To reduce the risk of exposing the outer surface of the shaft 304 to contaminants, and thereafter inserting the contaminated shaft 304 through the introducer sheath and into the blood supply, the anchor device 372 and contamination shield 374 may be used. In particular, the anchor device 372 may be configured to attach directly to an introducer sheath. Thereafter, the shaft 304 may pressed into the introducer sheath and the shaft 304 may be able to move relative to the anchor device 372. The contamination shield 374 can encompass the portion of the shaft 304 remaining outside the patient and introducer sheath, thereby reducing the risk that the shaft 304 will be exposed to contaminants. In some embodiments, when the shaft 304 is at a desired position (e.g., when the distal tip 360 is located inside the coronary sinus), the anchor device 372 may be selectively and/or releasably secured to the shaft 304. Such securement may substantially prevent the shaft 304 from moving relative to the anchor device 372, which may cause the shaft 304 to be prevented from either being advanced or being retracted until the anchor device 372 is selectively released from the shaft 304.

Figure 8:
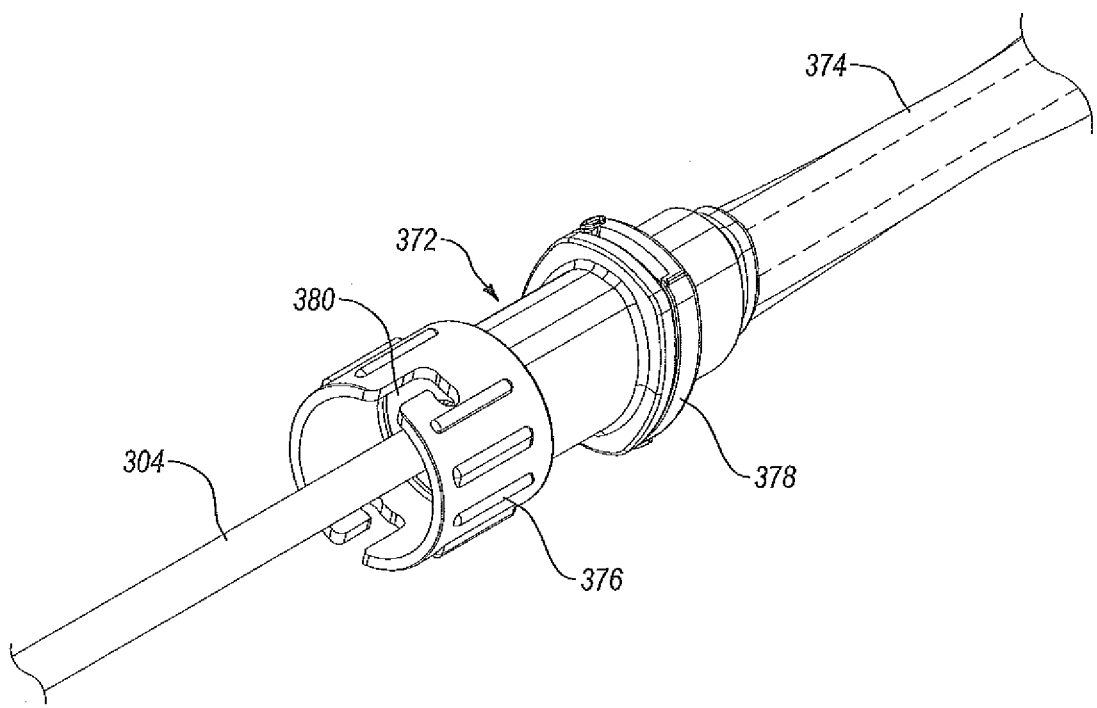
FIG. 8 illustrates an enlarged perspective view of the anchor device and contamination shield of the retrograde cardioplegia delivery catheter of FIG. 3.

Turning now to FIG. 8, an enlarged view of the anchor device 372 is provided. It should be appreciated that the anchor device 372 is merely one exemplary embodiment of a suitable anchor device, and that any number of devices may be used. In the illustrated embodiment, the anchor device 372 includes at least two components. In particular, in the illustrated embodiment, the anchor device 372 includes an introducer attachment 376 and a clamp 378. The introducer attachment 376 can be used to attach the anchor device 372 to an introducer sheath, while the clamp 378 may alone, or in combination with the introducer attachment 376, be used to clamp the anchor device 372 to the shaft 304.

An introducer sheath may have any number of connection mechanisms. One exemplary connection mechanism includes a post extending radially from an outer or interior surface of the introducer sheath. A distal end of the introducer attachment 376 may be sized to mate with the introducer sheath. For instance, the introducer attachment 376 may have an opening into which an end of the introducer sheath is positioned, or may have an exterior surface positioned within an opening of the introducer sheath. In FIG. 8, the introducer attachment 376 includes an L-shaped groove 380. Regardless of the manner in which the introducer sheath is received, the post from the introducer sheath may be inserted fully through the distal portion of the L-shaped groove 380. Following insertion of the introducer sheath in such a manner, the anchor device 372 can be rotated, thereby causing the post to pass into the proximal portion of the L-shaped groove 380. When positioned in the proximal portion of the groove 380, the anchor device 372 may be selectively secured to the introducer sheath movement of the anchor device 372 along its longitudinal axis can be substantially prevented. The L-shaped groove 380 may provide a bayonet-style attachment to the introducer sheath, however, any other suitable connection may be used.

In the illustrated embodiment, the anchor device includes a clamp 378 that may be attached to the proximal end of the introducer attachment 376. In at least some embodiments, the clamp 378 may be permitted to move relative to the introducer attachment 376. For instance, the clamp 378 may be at least partially rotatable relative to the introducer attachment. More particularly, by rotating the clamp 378, an engagement structure at the interface between the clamp 378 and the introducer attachment 376 may be activated. The engagement structure can engage the shaft 304 which extends through the anchor device 372. When engaged, the shaft 304 may be substantially prevented from moving relative to the anchor device 372.

One manner of activating an engagement structure by rotating the clamp 378 relative to the introducer attachment 376 is described in U.S. Pat. No. 5,279,597, issued on Jan. 18, 1994, and entitled "CATHETER COMPRESSION CLAMP," which patent is hereby expressly incorporated herein by this reference, in its entirety. In the referenced patent, a catheter clamp may include rotatable inner and outer members, with at least one protrusion that is compressed by a beveled interior sidewall.

Figure 9A:
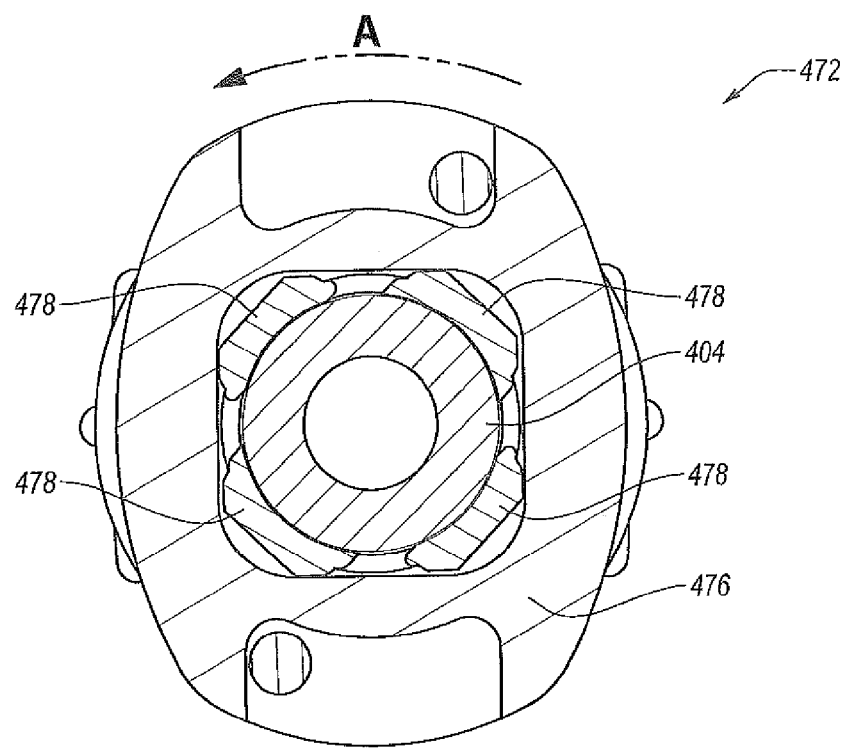
FIGS. 9A and 9B schematically illustrate an anchor device and method for anchoring the device to a catheter shaft.
Figure 9B:
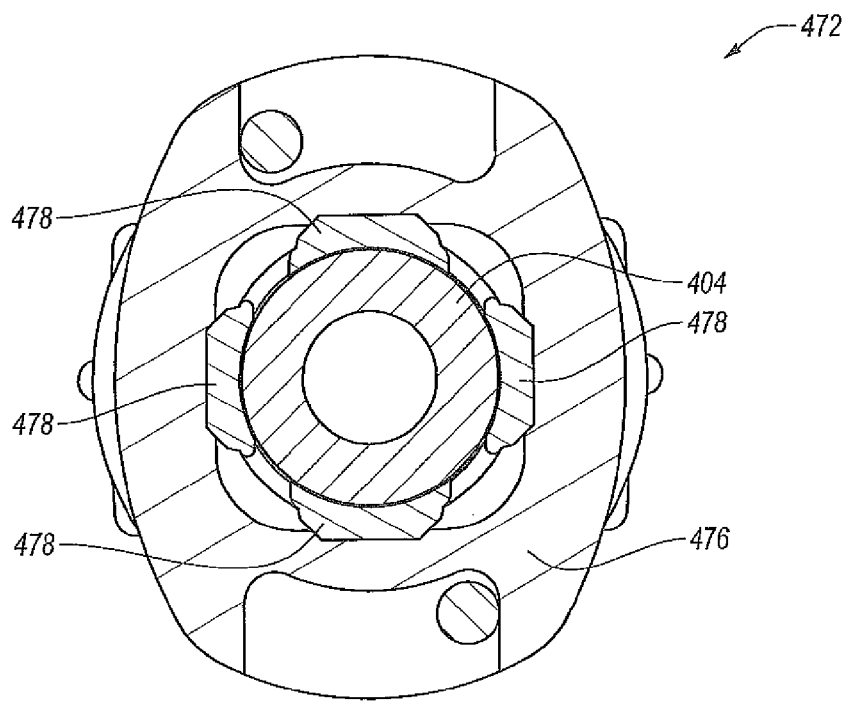

FIGS. 9A and 9B illustrate another exemplary manner in which an introducer attachment 376 may be used in connection with a clamp 378 to selectively lock the anchor device 372 in place relative to the shaft. More particularly, FIGS. 9A and 9B schematically illustrate a cross-section of a portion of an exemplary anchor device 472. In the illustrated embodiment, the anchor device 472 includes an outer ring 476 and an inner component 478. The outer ring 476 may represent a portion of the introducer attachment 376 or the clamp 378 of FIG. 8, and the inner component 478 may represent an opposing structure. The inner component 478 is illustrated in the form of two protrusions, however, it should be appreciated that such protrusions may instead be a ring, may be coupled to a ring, or may otherwise be secured relative to the outer ring 476. A shaft 404 extends through the interior of the inner component 478.

In some embodiments, the outer ring 476 can be rotated. For instance, the outer ring 478 may be rotated in the direction of Arrow A, so as to move from the position in FIG. 9A to the position in FIG. 9B. In FIG. 9A, it can be seen that the outer ring 476 is aligned with the inner component 478 such that the inner component 478 is positioned within a gap between the shaft 404 and the outer ring 476. However, upon rotating the outer ring 476, the gap may also rotate. Where the inner component 478 is angularly fixed relative to the shaft 404, the inner component 478 may not shift into the gap. Rather, an interior surface of the outer ring 478 may move over the inner component 478. In some embodiments, the inner component 478 is compressible. Consequently as the outer ring 476 rotates, it may compress the inner component 478. Compression of the inner component 478 may be used to, among other things, exert a radially inward direct force towards the shaft 404. The radially inward force may compress the shaft 404 in a manner that selectively locks the shaft 404 in place relative to the anchor device 472, and substantially prevented from moving longitudinally through the anchor device 472. By rotating the outer ring 476 in an opposite direction, the inner component 478 may decompress and the shaft 404 may be selectively release. The shaft 404 may then be free to move longitudinally relative to the anchor device 472.

A surgeon may desire to lock the shaft 404 relative to the anchor device 472 for any number of reasons. For instance, the shaft 404 may be a part of a retrograde cardioplegia delivery catheter as described herein. The catheter may be extended through a delivery device and into a patient so as to locate a desired component (e.g., an expandable member and/or distal tip) within the coronary sinus of the patient. Upon being positioning the catheter in such a manner, the catheter may remain in place for some time while a procedure is performed. For instance, a valve replacement may be performed. An example valve replacement is described in U.S. Pat. No. 5,558,644, issued on Sep. 24, 1996, and entitled "RETROGRADE DELIVERY CATHETER AND METHOD FOR INDUCING CARDIOPLEGIC ARREST," which application is expressly incorporated herein by this reference, in its entirety.

Once the catheter is in place, the surgeon may release the catheter to free his or her hands to perform the desired procedure. However, if the catheter is not held in place, the catheter may move within the coronary sinus, and may extend too far therein, or may be inadvertently pushed out from the coronary sinus. To guard against such occurrences, the expandable member of the catheter may be expanded to engage the sidewalls of the coronary sinus. The coronary sinus may, however, be relatively fragile such that high frictional forces between the coronary sinus and the expandable member are not desired. In such a case, the catheter may be locked in place using the anchor devices 372, 472 described herein, or using any other suitable device. The anchor device may effectively lock the catheter in place relative to the introducer sheath. The column stiffness of the catheter shaft may then be relied upon to maintain the catheter in the desired position.

Although the foregoing invention has been described in some detail by way of illustration and example, for purposes of clarity and understanding, certain changes and modifications will be obvious to those with skill in the art in view of the disclosure herein. The described embodiments are to be considered in all respects only as illustrative and not restrictive. Thus, all changes which come within the meaning and range of equivalency of the claims are to be embraced within their scope.

What is claimed is:

1. A retrograde delivery catheter for retrograde delivery of a fluid into a coronary sinus, the retrograde delivery catheter comprising:
   a flexible, elongated shaft having a proximal end and a distal end, the shaft having sufficient length and flexibility so that the proximal end may extend intraluminally through a patient such that when the proximal end is external to the patient, the distal end is positioned in the coronary sinus of the patient, the flexible, elongated shaft defining at least two lumens extending from about the proximal end toward the distal end;
   an atraumatic distal tip at about the distal end of the flexible, elongated shaft;
   an expandable member positioned at least proximate the distal end of the flexible, elongated shaft, the expandable member being configured to at least partially occlude the patient's coronary sinus; and
   a user interface coupled to the flexible, elongated shaft, the user interface being configured to control selective articulation of the distal end of the flexible, elongated shaft, wherein the user interface defines at least one pre-set articulation position of the distal end of the flexible, elongated shaft, wherein at the at least one pre-set articulation position, the flexible, elongated shaft defines multiple sections having differing curvature radii, wherein the multiple sections are positioned in end-to-end relationship to each other along the length of the catheter, the multiple sections having differing curvature radii include at least three sections, the at least three sections each having a different durometer, wherein a first section of the three sections comprises a first section curve radius and a first section deflection, wherein a second section of the three sections comprises a second section curve radius of between 18 cm and 40 cm and a second section deflection of 10 to 20 degrees, wherein a third section of the three sections comprises a third section curve radius of between 5 and 8 cm and a third section deflection of 85 to 95 degrees, wherein the first section curve radius is larger than the second section curve radius, wherein the first section deflection is less than the second section deflection, wherein the first section is proximal to the second section along the length of the catheter, and wherein the second section is proximal of the third section along the length of the catheter.

2. The retrograde delivery catheter recited in claim 1, wherein the flexible, elongated shaft has a predefined shape that includes an initial bend at the distal end.

3. The retrograde delivery catheter recited in claim 2, wherein the initial bend is in a range of about 2° to about 20° relative to a longitudinal axis of a proximal portion of the flexible, elongated shaft.

4. The retrograde delivery catheter recited in claim 2, wherein a first position of the user interface corresponds to the initial bend at the distal end of the flexible, elongated shaft.

5. The retrograde delivery catheter recited in claim 1, wherein the user interface defines at least:
   an engagement position, the engagement position corresponding to a stressed position of the user interface.

6. The retrograde delivery catheter recited in claim 1, wherein at the at least one pre-set articulation position, the atraumatic distal tip is in a range of about 75° to about 105° relative to a longitudinal axis of a proximal portion of the flexible, elongated shaft.

7. The retrograde delivery catheter recited in claim 1, further comprising:
   a pull-wire attached to the user interface and to the flexible, elongated shaft at about the distal end of the flexible, elongated shaft.

8. The retrograde delivery catheter recited in claim 7, wherein the pull-wire extends through a primary lumen of the at least two lumens.

9. The retrograde delivery catheter recited in claim 7, further comprising a reinforcement member, wherein the reinforcement member and pull-wire each extend through a primary lumen of the at least two lumens.

10. The retrograde delivery catheter recited in claim 7, wherein the pull-wire includes a jacket thereon.

11. The retrograde delivery catheter recited in claim 7, wherein the user interface includes a multi-position switch, the multi-position switch being linked to the pull-wire.

12. The retrograde delivery catheter recited in claim 11, wherein the multi-position switch moves at a ratio relative to movement of the pull-wire.

13. The retrograde delivery catheter recited in claim 1, wherein the user interface includes a switch configured to at least partially control selective articulation of the distal end of the flexible, elongated shaft.

14. The retrograde delivery catheter recited in claim 13, wherein the switch is a multi-position switch, the multi-position switch including:
- a first position corresponding to an insertion position of the distal end of the flexible, elongated shaft;
- a second position corresponding to an engagement position of the distal end of the flexible, elongated shaft; and
- a third position corresponding to a troubleshooting position of the distal end of the flexible, elongated shaft.

15. The retrograde delivery catheter recited in claim 13, wherein the switch is a multi-position switch, the multi-position switch including at least three positions, wherein at least one of the three positions is configured to be non-sustainable without user pressure on the switch.

16. The retrograde delivery catheter recited in claim 15, wherein the at least three positions include first, second and third positions, wherein the third position is non-sustainable and, without user pressure, reverts to the second position.

17. The retrograde delivery catheter recited in claim 16, wherein the first position and the second position are self-sustaining.

18. The retrograde delivery catheter recited in claim 16, wherein a plurality of self-sustaining positions exist between the first position and the second position.

19. The retrograde delivery catheter recited in claim 1, wherein the flexible, elongated shaft is configured to remain in-plane when selectively articulated by the user interface.

20. A retrograde delivery catheter for retrograde delivery of a fluid into a coronary sinus, the retrograde delivery catheter comprising:
- an elongated shaft having a proximal end and a distal end, the elongated shaft having sufficient length and flexibility so that the elongated shaft may extend intraluminally through a patient via a peripheral blood vessel such that when the proximal end is external to the patient, the distal end is positioned in the coronary sinus of the patient, wherein a distal portion of the elongated shaft is configured to be selectively articulated between at least two pre-determined curve profiles, the elongated shaft defining at least a fluid delivery lumen and an inflation lumen and a pressure sensing lumen, wherein the fluid delivery lumen is configured to accommodate fluid flow rates of at least 100 ml/minute;
- an atraumatic distal tip at the distal end of the elongated shaft, wherein the atraumatic distal tip comprises a durometer of approximately 25 Shore D;
- an expandable member positioned at the distal portion of the elongated shaft proximate the atraumatic distal tip, the expandable member being inflatable to at least partially occlude the coronary sinus, wherein the inflation lumen passes along the elongated shaft from the proximal end to the expandable member and is in fluid connection with the expandable member;
- a pressure port positioned on the distal portion of the elongated shaft at a location distal of the expandable member, the pressure port in fluid communication with the pressure lumen; and
- at least one fluid outlet port, the at least one fluid outlet port being in communication with the fluid delivery lumen, the outlet port positioned on the distal portion of the elongated shaft at a location distal to the expandable member, wherein the elongated shaft includes at least three sections having differing durometer, wherein the at least three sections are positioned in end-to-end relationship to each other along the length of the catheter, wherein a first section of the three sections comprises a first section curve radius and a first section deflection, wherein a second section of the three sections comprises a second section curve radius of between 18 cm and 40 cm and a second section deflection of 10 to 20 degrees, wherein a third section of the three sections comprises a third section curve radius of between 5 and 8 cm and a third section deflection of 85 to 95 degrees, wherein the first section curve radius is larger than the second section curve radius, wherein the first section deflection is less than the second section deflection, wherein the first section is proximal to the second section along the length of the catheter, and wherein the second section is proximal of the third section along the length of the catheter.

21. The retrograde delivery catheter of claim 20, wherein the elongated shaft is configured to selectively articulate, and wherein interfaces between the at least three sections define inflection points for the selective articulation of the elongated shaft.

22. The retrograde delivery catheter of claim 20, wherein the at least three sections having a durometer varying between about 20 and about 80 shore D.

23. The retrograde delivery catheter of claim 20, further comprising:
- a user interface coupled to the elongated shaft, the user interface being configured to control selective articulation of the distal end of the elongated shaft, wherein the user interface defines at least one pre-set articulation position of the distal end of the elongated shaft.

24. The retrograde delivery catheter of claim 23, further comprising:
- a pull-wire extending through the elongated shaft from the user interface to the distal end of the elongated shaft, wherein a longitudinally directed force applied to the pull-wire articulates the distal end of the elongated shaft.

25. The retrograde delivery catheter of claim 20, wherein the expandable member comprises a balloon having a maximum inflated diameter of up to 17 mm and an uninflated diameter of less than 6 mm.

26. The retrograde delivery catheter of claim 20, wherein the at least one fluid outlet port is positioned on the elongated shaft at a position between the atraumatic distal tip and the expandable member.

27. A retrograde fluid delivery catheter adapted to be advanced into a coronary sinus of a patient's heart for retrograde delivery of a fluid, the retrograde delivery catheter comprising:
- an elongated shaft having a proximal end and a distal end, the elongated shaft having sufficient length and flexibility so that the proximal end may extend intraluminally through a patient's peripheral vein when the distal end is positioned in the coronary sinus, wherein the elongated shaft includes at least three sections having differing durometer, wherein the at least three sections are positioned in end-to-end relationship to each other along the length of the catheter, wherein a first section of the three sections comprises a first section curve radius and a first section deflection, wherein a second section of the three sections comprises a second section curve radius of between 18 cm and 40 cm and a second section deflection of 10 to 20 degrees, wherein a third section of the three sections comprises a third section curve radius of between 5 and 8 cm and a third section deflection of 85 to 95 degrees, wherein the first section curve radius is larger than the second section curve radius, wherein the first section deflection is less than the second section deflection, wherein the first section is proximal to the second section along the length of the catheter, and wherein the second section is proximal of the third section along the length of the catheter, and the elongated shaft further includes:

at least two layers, the at least two layers including an outer shell and an interior reinforcement member;

a fluid delivery lumen surrounded by the outer shell and surrounded by the interior reinforcement member; and an inflation lumen within the outer shell of the elongated shaft, wherein the inflation lumen is positioned radially outside of the interior reinforcement member;

an expandable member at least proximate the distal end, the expandable member being configured to at least partially occlude the patient's coronary sinus, the expandable member being in fluid communication with the inflation lumen within the elongated shaft; and a fluid delivery port, the fluid delivery port being in fluid communication with the fluid delivery lumen, the fluid delivery lumen being adapted to deliver a fluid to the fluid delivery port, wherein the fluid delivery port is positioned on the elongated shaft at a location distal to the expandable member.

28. The retrograde fluid delivery catheter of claim 27, wherein the distal end of the shaft includes a distal tip configured to position the expandable member in the patient's coronary sinus when the proximal end of the elongate shaft extends through the patient's peripheral vein.

29. The retrograde fluid delivery catheter of claim 27, wherein the at least three sections having a durometer varying between about 20 and about 80 Shore D.

30. The retrograde fluid delivery catheter of claim 27, wherein the elongated shaft is configured to selectively articulate, and wherein interfaces between the at least three sections define inflection points for the selective articulation of the elongated shaft.

31. The retrograde fluid delivery catheter of claim 27, wherein the elongated shaft further comprises a pressure monitoring lumen.

32. The retrograde fluid delivery catheter of claim 31, wherein the elongated shaft comprises:

at least one pressure monitoring port at least proximate the distal end of the elongated shaft, wherein the at least one pressure port is in fluid communication with the pressure lumen, and the delivery port and the at least one pressure port are positioned on the elongated shaft at a position distal of the expandable member; and at least one inflation port in fluid communication with the inflation lumen, the at least one inflation port providing inflation fluid to the expandable member.

33. The retrograde fluid delivery catheter of claim 32, wherein:

the fluid delivery lumen is a cardioplegia delivery lumen that extends through the elongated shaft from the proximal end of the elongated shaft to the fluid delivery port;

the pressure monitoring lumen extends through the elongated shaft from the proximal end of the elongated shaft to the at least one pressure port; and the inflation lumen extends through the elongated shaft from the proximal end of the elongated shaft to the at least one inflation port.

34. The retrograde fluid delivery catheter of claim 27, further comprising a pull-wire, wherein the pull-wire extends from about the proximal end of the elongated shaft to the distal end of the elongated shaft.

35. The retrograde fluid delivery catheter of claim 34, wherein a longitudinally directed force applied to the pull-wire articulates the distal end of the elongated shaft.

36. The retrograde delivery catheter of claim 27, wherein the interior reinforcement member includes a braided tube.

37. The retrograde delivery catheter of claim 27, wherein the interior reinforcement member is made of a material having a higher echogenicity than a material of the outer shell.

38. The retrograde delivery catheter of claim 27, wherein the fluid delivery lumen is a configured to deliver cardioplegia fluid at a volumetric flow rate of at least 100 ml/min.

* * * * *